United States Patent
Friedman et al.

(10) Patent No.: US 10,137,239 B2
(45) Date of Patent: *Nov. 27, 2018

(54) SYSTEMS AND METHODS FOR MONITORING TIME BASED PHOTO ACTIVE AGENT DELIVERY OR PHOTO ACTIVE MARKER PRESENCE

(71) Applicant: Avedro, Inc., Waltham, MA (US)

(72) Inventors: Marc D. Friedman, Needham, MA (US); Pavel Kamaev, Lexington, MA (US); David Muller, Boston, MA (US); Radha Pertaub, Watertown, MA (US); Ronald Scharf, Waltham, MA (US); Evan Sherr, Ashland, MA (US); David Usher, Waltham, MA (US)

(73) Assignee: Avedro, Inc., Waltham, MA (US)

( * ) Notice: Subject to any disclaimer, the term of this patent is extended or adjusted under 35 U.S.C. 154(b) by 648 days.

This patent is subject to a terminal disclaimer.

(21) Appl. No.: 14/696,672

(22) Filed: Apr. 27, 2015

(65) Prior Publication Data
US 2015/0265762 A1    Sep. 24, 2015

Related U.S. Application Data

(63) Continuation of application No. 13/488,097, filed on Jun. 4, 2012, now Pat. No. 9,020,580.
(Continued)

(51) Int. Cl.
*A61B 5/00* (2006.01)
*A61M 5/00* (2006.01)
(Continued)

(52) U.S. Cl.
CPC .............. *A61M 5/007* (2013.01); *A61B 3/10* (2013.01); *A61B 3/107* (2013.01); *A61B 3/135* (2013.01);
(Continued)

(58) Field of Classification Search
CPC ................ A61L 3/10; A61L 3/00; A61M 5/07
See application file for complete search history.

(56) References Cited

U.S. PATENT DOCUMENTS

| | | |
|---|---|---|
| 3,169,459 A | 2/1965 | Friedberg et al. |
| 4,034,750 A | 7/1977 | Seiderman |

(Continued)

FOREIGN PATENT DOCUMENTS

| | | |
|---|---|---|
| DE | 102008046834 | 3/2010 |
| EP | 1285679 | 2/2003 |

(Continued)

OTHER PUBLICATIONS

Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
(Continued)

*Primary Examiner* — Joel F Brutus
(74) *Attorney, Agent, or Firm* — McDonnell Boehnen Hulbert & Berghoff LLP

(57) ABSTRACT

Devices and approaches for monitoring time based photo active agent delivery or photo active marker presence in an eye. A monitoring system is provided for measuring the presence of a photo active marker by illuminating the eye so as to excite the photo-active marker and then observing characteristic emission from the photo active marker. Example systems incorporate Scheimpflug optical systems or slit lamp optical systems to observe cross sectional images of an eye to monitor instantaneous distribution, diffusion pattern, and rate of uptake of a photo active agent applied to an eye. Systems and methods further allow for utilizing the monitored distribution of photo active agent in the eye as feedback for a cross-linking system.

20 Claims, 23 Drawing Sheets

Related U.S. Application Data

(60) Provisional application No. 61/492,553, filed on Jun. 2, 2011, provisional application No. 61/566,976, filed on Dec. 5, 2011, provisional application No. 61/594,796, filed on Feb. 3, 2012.

(51) Int. Cl.
| | |
|---|---|
| *A61B 3/10* | (2006.01) |
| *A61N 5/06* | (2006.01) |
| *A61B 3/107* | (2006.01) |
| *A61B 3/135* | (2006.01) |
| *A61F 9/007* | (2006.01) |
| *A61K 49/00* | (2006.01) |
| *A61B 3/14* | (2006.01) |
| *A61F 9/008* | (2006.01) |
| *A61N 5/067* | (2006.01) |
| *A61M 37/00* | (2006.01) |

(52) U.S. Cl.
CPC ............ *A61B 3/145* (2013.01); *A61B 5/0071* (2013.01); *A61F 9/008* (2013.01); *A61F 9/0079* (2013.01); *A61K 49/006* (2013.01); *A61N 5/062* (2013.01); *A61B 5/0066* (2013.01); *A61F 2009/00851* (2013.01); *A61F 2009/00872* (2013.01); *A61F 2009/00893* (2013.01); *A61M 37/0092* (2013.01); *A61N 2005/067* (2013.01); *A61N 2005/0626* (2013.01); *A61N 2005/0661* (2013.01)

(56) References Cited

U.S. PATENT DOCUMENTS

| | | |
|---|---|---|
| 4,161,013 A | 7/1979 | Grodzinsky et al. |
| 4,326,529 A | 4/1982 | Doss et al. |
| 4,381,007 A | 4/1983 | Doss |
| 4,665,913 A | 5/1987 | L'Esperance, Jr. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,098,426 A | 3/1992 | Sklar et al. |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,450,144 A | 9/1995 | Nun |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,608,472 A | 3/1997 | Szirth et al. |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,280,436 B1 | 8/2001 | Freeman et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,394,999 B1 | 5/2002 | Williams et al. |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Shahinian, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,237,898 B1 | 7/2007 | Hohla et al. |
| 7,270,658 B2 | 9/2007 | Woloszko et al. |
| 7,302,189 B2 | 11/2007 | Kawahata |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,871,378 B1 | 1/2011 | Chou et al. |
| 7,898,656 B2 | 3/2011 | Yun et al. |
| 7,935,058 B2 | 5/2011 | Dupps, Jr. et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 8,574,277 B2 | 11/2013 | Muller et al. |
| 8,715,273 B2 | 5/2014 | Thyzel |
| 8,995,618 B2 | 3/2015 | Gertner |
| 9,005,261 B2 | 4/2015 | Brinkmann |
| 2001/0041856 A1 | 11/2001 | McDaniel |
| 2001/0047012 A1 | 11/2001 | Desantis, Jr. |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0042638 A1 | 4/2002 | Iezzi et al. |
| 2002/0049437 A1 | 4/2002 | Silvestrini |
| 2002/0099363 A1 | 7/2002 | Woodward et al. |
| 2002/0159618 A1* | 10/2002 | Freeman ............... A61B 3/13 382/128 |
| 2002/0164379 A1 | 11/2002 | Nishihara et al. |
| 2003/0018255 A1 | 1/2003 | Martin et al. |
| 2003/0030908 A1 | 2/2003 | Cheng et al. |
| 2003/0135122 A1 | 7/2003 | Bambot et al. |
| 2003/0175259 A1 | 9/2003 | Karageozian et al. |
| 2003/0189689 A1 | 10/2003 | Rathjen |
| 2003/0208190 A1 | 11/2003 | Roberts et al. |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |

(56) References Cited

U.S. PATENT DOCUMENTS

| | | |
|---|---|---|
| 2004/0243160 A1 | 12/2004 | Shiuey et al. |
| 2004/0254520 A1 | 12/2004 | Porteous et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0187599 A1 | 8/2005 | Sharkey et al. |
| 2005/0271590 A1 | 12/2005 | Schwartz et al. |
| 2006/0058592 A1 | 3/2006 | Bouma et al. |
| 2006/0106371 A1 | 5/2006 | Muhlhoff et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195074 A1 | 8/2006 | Bartoli |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0028928 A1 | 2/2007 | Peyman |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0090153 A1 | 4/2007 | Naito et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203478 A1 | 8/2007 | Herekar |
| 2007/0203547 A1 | 8/2007 | Costello et al. |
| 2007/0244470 A1 | 10/2007 | Barker, Jr. et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0033408 A1 | 2/2008 | Bueler et al. |
| 2008/0063627 A1 | 3/2008 | Stucke et al. |
| 2008/0114283 A1* | 5/2008 | Mattson ............ A61K 9/0048 604/20 |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps, Jr. et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | de Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Ornberg et al. |
| 2010/0210996 A1 | 8/2010 | Peyman |
| 2010/0271593 A1 | 10/2010 | Filar |
| 2010/0286156 A1 | 11/2010 | Pinelli |
| 2010/0317588 A1 | 12/2010 | Shoseyov et al. |
| 2010/0318017 A1 | 12/2010 | Lewis et al. |
| 2011/0044902 A1 | 2/2011 | Weiner et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0125076 A1 | 5/2011 | Kraft et al. |
| 2011/0152219 A1 | 6/2011 | Stagni |
| 2011/0190742 A1 | 8/2011 | Anisimov |
| 2011/0202114 A1 | 8/2011 | Kessel et al. |
| 2011/0208300 A1 | 8/2011 | de Juan, Jr. et al. |
| 2011/0237999 A1 | 9/2011 | Muller et al. |
| 2011/0264082 A1 | 10/2011 | Mrochen et al. |
| 2011/0288466 A1 | 11/2011 | Muller et al. |
| 2011/0301524 A1 | 12/2011 | Bueler et al. |
| 2012/0083772 A1* | 4/2012 | Rubinfeld ............ A61F 9/0079 606/4 |
| 2012/0140238 A1 | 6/2012 | Horn et al. |
| 2012/0203051 A1 | 8/2012 | Brooks et al. |
| 2012/0203161 A1 | 8/2012 | Herekar |
| 2012/0209051 A1 | 8/2012 | Blumenkranz et al. |
| 2012/0215155 A1 | 8/2012 | Muller et al. |
| 2012/0283621 A1 | 11/2012 | Muller |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2013/0245536 A1 | 9/2013 | Friedman et al. |
| 2013/0310732 A1 | 11/2013 | Foschini et al. |
| 2014/0066835 A1 | 3/2014 | Muller et al. |
| 2014/0194957 A1 | 7/2014 | Rubinfeld et al. |
| 2014/0249509 A1 | 9/2014 | Rubinfeld et al. |
| 2014/0276361 A1 | 9/2014 | Herekar et al. |
| 2014/0277431 A1 | 9/2014 | Herekar et al. |
| 2014/0343480 A1 | 11/2014 | Kamaev et al. |
| 2014/0368793 A1 | 12/2014 | Friedman et al. |
| 2015/0085252 A1 | 3/2015 | Fujimura et al. |
| 2016/0139390 A1 | 5/2016 | Bukshtab et al. |
| 2016/0175442 A1 | 6/2016 | Kamaev et al. |

FOREIGN PATENT DOCUMENTS

| | | |
|---|---|---|
| EP | 1561440 | 8/2005 |
| EP | 1790383 | 5/2007 |
| EP | 2253321 | 11/2010 |
| IT | MI2010A001236 | 5/2010 |
| JP | 2000/262476 | 9/2000 |
| KG | 1376 | 8/2011 |
| RU | 2086215 | 8/1997 |
| RU | 2098057 | 12/1997 |
| RU | 2121825 | 11/1998 |
| RU | 2127099 | 3/1999 |
| RU | 2127100 | 3/1999 |
| RU | 2309713 | 11/2007 |
| RU | 2359716 | 6/2009 |
| RU | 2420330 | 6/2011 |
| RU | 2428152 | 9/2011 |
| RU | 2456971 | 7/2012 |
| WO | 93/16631 | 9/1993 |
| WO | 94/03134 | 2/1994 |
| WO | 00/74648 | 12/2000 |
| WO | 01/58495 | 8/2001 |
| WO | 03/061696 | 7/2003 |
| WO | 2004/052223 | 6/2004 |
| WO | 2005/110397 | 11/2005 |
| WO | 2006/012947 | 2/2006 |
| WO | 2006/128038 | 11/2006 |
| WO | 2007/001926 | 1/2007 |
| WO | 2007/053826 | 5/2007 |
| WO | 2007/081750 | 7/2007 |
| WO | 2007/120457 | 10/2007 |
| WO | 2007/128581 | 11/2007 |
| WO | 2007/139927 | 12/2007 |
| WO | 2007/143111 | 12/2007 |
| WO | 2008/000478 | 1/2008 |
| WO | 2008/052081 | 5/2008 |
| WO | 2008/095075 | 8/2008 |
| WO | 2009/042159 | 4/2009 |

(56) References Cited

FOREIGN PATENT DOCUMENTS

| WO | 2009/073213 | 6/2009 |
|---|---|---|
| WO | 2009/114513 | 9/2009 |
| WO | 2009/146151 | 12/2009 |
| WO | 2010/011119 | 1/2010 |
| WO | 2010/015255 | 2/2010 |
| WO | 2010/023705 | 3/2010 |
| WO | 2010/039854 | 4/2010 |
| WO | 2010/093908 | 8/2010 |
| WO | 2011/019940 | 2/2011 |
| WO | 2011/050360 | 4/2011 |
| WO | 2011/116306 | 9/2011 |
| WO | 2012/004726 | 1/2012 |
| WO | 2012/047307 | 4/2012 |
| WO | 2012/149570 | 11/2012 |
| WO | 2012/158991 | 11/2012 |
| WO | 2012/174453 | 12/2012 |
| WO | 2013/062910 | 5/2013 |
| WO | 2013/148713 | 10/2013 |
| WO | 2013/148895 | 10/2013 |
| WO | 2013/149075 | 10/2013 |
| WO | 2014/081875 | 5/2014 |
| WO | 2014/145666 | 9/2014 |
| WO | 2014/202736 | 12/2014 |
| WO | 2016069628 | 5/2016 |

OTHER PUBLICATIONS

Wollensak G., "Crosslinking Treatment of Progressive Keratoconus: New Hope," Current Opinion in Ophthalmology, vol. 17(4), pp. 356-360; Aug. 2006 (5 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).

Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).

Wong, J. et al., "Post-Lasik ectasia: PRK following previous stablization and effective management with Riboflavin / ultraviolet A-induced corneal cross-linking," Association for Research in Vision and Ophthalmology, 2006 (1 page).

Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).

Yang N., Oster G. Dye-sensitized photopolymerization in the presence of reversible oxygen carriers. J. Phys. Chem. 74, 856-860 (1970) (5 pages).

Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program No. 1073, poster board No. A109.

Zhang, Y. et al., "Effects of Ultraviolet-A and Riboflavin on the Interaction of Collagen and Proteoglycans during Corneal Cross-linking", Journal of Biological Chemistry, vol. 286, No. 15, dated Apr. 15, 2011 (pp. 13011-13022).

Zderic V., et al., "Drug Delivery Into the Eye With the Use of Ultrasound," J. Ultrasound Med, vol. 23(10), pp. 1349-1359; Oct. 2004 (11 pages).

Zderic V., et al., "Ultrasound-enhanced Transcorneal Drug Delivery," Cornea vol. 23, No. 8, pp. 804-811; Nov. 2004 (8 pages).

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164.

Acosta A. et al., "Corneal Stroma Regeneration in Felines After Supradescemetic Keratoprothesis Implantation," Cornea, vol. 25, No. 7, pp. 830-838; Aug. 2006.

Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html.

Baier J. et al., "Singlet Oxygen Generation by UVA Light Exposure of Endogenous Photosensitizers," Biophysical Journal, vol. 91(4), pp. 1452-1459; Aug. 15, 2006.

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969.

Barbarino, S. et al., "Post-LASIK ectasia: Stabilization and Effective Management with Riboflavin / ultraviolet A-induced collagen cross-linking," Association for Research in Vision and Ophthalmology, 2006.

Berjano E., et al., "Radio-Frequency Heating of the Cornea: Theoretical Model and In Vitro Experiments," IEEE Transactions on Biomedical Engineering, vol. 49, No. 3, pp. 196-205; Mar. 2002.

Berjano E., et al., "Ring Electrode for Radio-frequency Heating of the Cornea: Modelling and in vitro Experiments," Medical & Biological Engineering & Computing, vol. 41, pp. 630-639; Jun. 2003.

Brüel, A., "Changes in Biomechanical Properties, Composition of Collagen and Elastin, and Advanced Glycation Endproducts of the Rat Aorta in Relation to Age," Atherosclerosis 127, Mar. 14, 1996.

Burke, JM et al., Abstract for "Retinal proliferation in response to vitreous hemoglobin or iron", Investigative Ophthalmology & Visual Science, May 1981, 20(5), pp. 582-592.

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238.

Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008.

Chandonnet, "CO2 Laser Annular Thermokeratoplasty: A Preliminary Study," Lasers in Surgery and Medicine, vol. 12, pp. 264-273; 1992.

Chace, KV. et al., Abstract for "The role of nonenzymatic glycosylation, transition metals, and free radicals in the formation of collagen aggregates", Arch Biochem Biophys., Aug. 1, 1991, 288(2), pp. 473-480.

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011.

Corbett M., et al., "Effect of Collagenase Inhibitors on Corneal Haze after PRK," Exp. Eye Res., vol. 72, Issue 3, pp. 253-259; Jan. 2001.

Coskenseven E. et al., "Comparative Study of Corneal Collagen Cross-linking With Riboflavin and UVA Irradiation in Patients With Keratoconus," Journal of Refractive Surgery, vol. 25, issue 4, pp. 371-376; Apr. 2009.

"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011.

Ehlers W., et al., "Factors Affecting Therapeutic Concentration of Topical Aminocaproic Acid in Traumatic Hyphema," Investigative Ophthalmology & Visual Science, vol. 31, No. 11, pp. 2389-2394; Nov. 1990.

Erskine H., "Avedro Becomes Sponsor of US FDA Clinical Trials of Corneal Collagen Crosslinking," Press Release, Mar. 16, 2010 (1 page).

Fite et al., "Noninvasive Multimodal Evaluation of Bioengineered Cartilage Constructs Combining Time-Resolved Fluorescence and Ultrasound Imaging." Tissue Eng: Part C vol. 17, No. 4, 2011.

(56) References Cited

OTHER PUBLICATIONS

Friedman, M. et al. "Advanced Corneal Cross-Linking System with Fluorescence Dosimetry", Journal of Ophthalmology, vol. 2012, Article ID 303459, dated May 7, 2012.

Frucht-Pery, et al. "Iontophoresis—gentamicin delivery into the rabbit cornea, using a hydrogel delivery probe," Jun. 20, 2003.

Gibson, Q. et al., "The Oxidation of Reduced Flavin Mononucleotide by Molecular Oxygen," Biochem. J. (1962) 83, 368-377.

Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).

Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009.

Gravitz L., "Laser Show in the Surgical Suite: Lasers and a century-old dye could supplant needles and thread;" technology review, MIT, Mar./Apr. 2009; retrieved from http://www.technologyreview.com/biomedicine/22088/?nlid=1767, on Sep. 26, 2011.

Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009.

Hammer Arthur et al., "Corneal Biomechanical Properties at different Corneal Cross-Linking (CXL) Irradiances," IOVS, May 2014, vol. 55, No. 5, pp. 2881-2884.

Hitzenberger et al., "Birefringence Properties of the Human Cornea Measured With Polarization Sensitive Optical Coherence Tomography," Bull. Soc. Beige Ophtalmol., 302, 153-168, 2006.

Holmström, B. et al., "Riboflavin as an Electron Donor in Photochemical Reactions," 1867-1871, Nov. 29, 1960.

How to Use Definity: "Frequently Asked Questions;" retrieved from http://www.definityimaging.com/how-faq.html, on Sep. 26, 2011 (3 pages) (date unknown, prior to Apr. 26, 2010).

IMEX, "KXL System: Crosslinking Para Cirugia Corneal Bibliografia Cientifica," Product Literature, Nov. 23, 2010.

Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).

Kampik D. et al., "Influence of Corneal Collagen Crosslinking With Riboflavin and Ultraviolet-A Irradiation on Excimer Laser Surgery," Investigative Ophthalmology & Visual Science, vol. 51, No. 8, pp. 3929-3934; Aug. 2010.

Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.

Kanellopoulos, A. J., "Keratoconus management: UVA-induced collagen cross-linking followed by a limited topo-guided surface excimer ablation," American Academy of Ophthalmology, 2006 (25 pages).

Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).

Kissner Anja, et al., "Pharmacological Modification of the Epithelial Permeability by Benzalkonium Chloride in UVA/Riboflavin Corneal Collagen Cross-Linking," Current Eye Research 35(8), pp. 715-721; Mar. 2010 (7 pages).

Koller, T. et. Al., "Complication and failure rates after corneal crosslinking," Journal Cataract and refractive surgery, vol. 35, No. 8, Aug. 2009, pp. 1358-1362.

Koller T., et al., "Therapeutische Quervernetzung der Homhaut mittels UVA and Riboflavin: Therapeutic Cross-Linking of the Cornea Using Riboflavin/UVA," Klinische Monatsblätter für Augenheilkunde, vol. 224, No. 9, pp. 700-706; Sep. 2007 (7 pages).

Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).

Krueger, Ronald R., "Rapid VS Standard Collagen CXL with Equivalent Energy Dosing," presentation slides; available at http://www.slideshare.net/logen/krueger-herekar-rapid-cross-linking (date unknown, prior to Nov. 9, 2009) (26 pages).

Massey, V., "Activation of Molecular Oxygen by Flavins and Flavoproteins," The Journal of Biological Chemistry vol. 269, No. 36, Issue of Sep. 9, pp. 22459-22462, 1994 (4 pages).

Marzouky, et. al., Tensioactive-mediated Transepithelial Corneal Cross-linking—First Laboratory Report, European Ophthalmic Review, 2009, 3(2), pp. 67-70.

Lee et al., "Spectrally filtered Raman / Thomson scattering using a rubidium Vapor filter ", AIAA J. 40, pp. 2504-2510 (2002).

Li, C. et al."Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).

Li, C. et al. "Noncontact All-Optical Measurement of Corneal Elasticity." Optics Letters. vol. 37, No. 10, May 15, 2012 (pp. 1625-1627).

Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).

Meek, K.M. et al. "The Cornea and Scleera", Collagen: Structure and Mechanics, Chapter 13, pp. 359-396, 2008 (38 pages).

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).

Muller L., et al., "The Specific Architecture of the Anterior Stroma Accounts for Maintenance of Corneal Curvature," Br. J. Opthalmol., vol. 85, pp. 437-443; Apr. 2001 (8 pages).

Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).

Naoumidi T., et al., "Two-Year Follow-up of Conductive Keratoplasty for the Treatment of Hyperopic Astigmatism," J. Cataract Refract. Surg., vol. 32(5), pp. 732-741; May 2006 (10 pages).

Nesterov, A. P. "Transpalpebralny Tonometr Dlya Izmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.

O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).

O.V. Shilenskaya et al., "Vtorichnaya katarakta posle implantatsii myagkikh IOL," [online] Aug. 21, 2008 [retrieved Apr. 3, 2013] Retrieved from the Internet: <URL:http://www.reper.ru/rus/index.php?catid=210> (4 pages).

Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).

Pallikaris I., et al., "Long-term Results of Conductive Keratoplasty for low to Moderate Hyperopia," J. Cataract Refract. Surg., vol. 31(8), pp. 1520-1529; Aug. 2005 (10 pages).

Pinelli, R. "Corneal Cross-Linking with Riboflavin: Entering a New Era in Ophthalmology." Ophthalmology Times Europe. vol. 2, No. 7, Sep. 1, 2006, [online], [retrieved on May 20, 2013]. Retrieved from the Internet: <URL: http://www.oteurope.com/ophthalmologytimeseurope/Cornea/Corneal-cross-linking-with-riboflavin-entering-a-n/ArticleStandard/Article/detail/368411> (3 pages).

Pinelli R., et al., "C3-Riboflavin Treatments: Where Did We Come From? Where Are We Now?" Cataract & Refractive Surgery Today Europe, Summer 2007, pp. 36-46; Jun. 2007 (10 pages).

Pinelli, R., "Panel Discussion: Epithelium On/Off, Corneal abrasion for CCL contra", presented at the 3° International Congress of Corneal Cross Linking on Dec. 7-8, 2007 in Zurich (36 pages).

Roberto Pinelli et al, "Transepithelial Tensioactive Mediated CXL", Cataract & Refractive Surgery Today Europe, p. 1, URL: http://bmctoday.net/crstodayeurope/pdfs/0409_09.pdf, XP055158069.

Pinelli R., "Resultados de la Sociedad de Cirugia Refractiva Italiana (SICR) utilizando el C3-R" presented at the Istitutor Laser Microchirurgia Oculare in 2007 in Italy (23 pages).

(56) References Cited

OTHER PUBLICATIONS

Pinelli et al., "Tensioactive-mediated Transepithelial Corneal Cross-linking—First Laboratory Report", 2009, European Ophthalmic Review, 3(2), pp. 67-70.

Pinelli R., "The Italian Refractive Surgery Society (SICR) results using C3-R" presented Jun. 22-23, 2007 in Italy (13 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).

Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).

Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).

Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].

Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

Rocha K., et al., "Comparative Study of Riboflavin-UVA Cross-linking and "Flash-linking" Using Surface Wave Elastometry," Journal of Refractive Surgery, vol. 24 Issue 7, pp. S748-S751; Sep. 2008 (4 pages).

Rolandi et al., "Correlation of Collagen-Linked Fluorescence and Tendon Fiber Breaking Time." Gerontology 1991;27:240-243 (4 pages).

RxList: "Definity Drug Description;" The Internet Drug Index, revised Jun. 16, 2008, retrieved from http://www.rxlist.com/definity-drug.htm, on Sep. 26, 2011 (4 pages).

Saleh et al. "Fundamentals of Photonics" 1991, pp. 74-77.

Scarcelli, G. et al., "Brillouin Optical Microscopy for Corneal Biomechanics", Investigative Ophthalmology & Visual Science, Jan. 2012, vol. 53, No. 1, pp. 185-190 (6 pages).

Sheehan M., et al., "Illumination System for Corneal Collagen Crosslinking," Optometry and Vision Science, vol. 88, No. 4, pp. 512-524; Apr. 2011 (13 pages).

Shell, J., "Pharmacokinetics of Topically Applied Ophthalmic Drugs," Survey of Ophthalmology, vol. 26, No. 4, pp. 207-218; Jan.-Feb. 1982 (12 pages).

Sobol E N et al, "Correction of Eye Refraction by Nonablative Laser Action on Thermomechanical Properties of Cornea and Sclera", Quantum Electronics, Turpion Ltd., London, GB, (Oct. 2002), vol. 32, No. 10, ISSN 1063-7818, pp. 909-912, XP001170947 [A] 1.

Song P., Metzler D. "Photochemical Degradation of Flavins—IV. Studies of the Anaerobic Photolysis of Riboflavin." Photochemistry and Photobiology, vol. 6, pp. 691-709, 1967 (21 pages).

Sonoda S., "Gene Transfer to Corneal Epithelium and Keratocytes Mediated by Ultrasound with Microbubbles," Investigative Ophthalmology & Visual Science, vol. 47, No. 2, pp. 558-564; Feb. 2006 (7 pages).

Spoerl E., et al., "Artificial Stiffening of the Cornea by Induction of Intrastromal Cross-links," Der Ophthalmologe, vol. 94, No. 12, pp. 902-906; Dec. 1997 (5 pages).

Spoerl E., et al., "Induction of Cross-links in Corneal Tissue," Experimental Eye Research, vol. 66, Issue 1, pp. 97-103; Jan. 1998 (7 pages).

Spoerl E. et al., "Safety of UVA-Riboflavin Cross-Linking of the Cornea," Cornea, vol. 26, No. 4, pp. 385-389; May 2007 (5 pages).

Spoerl E., et al., "Techniques for Stiffening the Cornea," Journal of Refractive Surgery, vol. 15, Issue 6, pp. 711-713; Nov.-Dec. 1999 (4 pages).

Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).

"Tahzib N.G. et al., ""Recurrent intraocular inflamation after implantation of the Artiflex phakic intraocular lens for the correction of high myopia,"" J Cataract Refract Surg, Aug. 2006; 32(8)1388-91, (abstract) [online] [Retrived Mar. 4, 2013] Retrieved from PubMed, PMID: 16863981".

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

Thornton, I. et. al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.

Thornton et al (Investigative Ophthalmology and Visual Science, Mar. 2009, vol. 50, No. 3, pp. 1227-1233).

Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).

Tomlinson et al. (Investigative Opthalmology and Visual Science 2006, 47 (10), 4309, 4315.

Trembly et al., "Microwave Thermal Keratoplasty for Myopia: Keratoscopic Evaluation in Porcine Eyes," Journal of Refractive Surgery, vol. 17, No. 6, pp. 682-688; Nov./Dec. 2001 (8 pages).

Turgunbaev N.A. et al. Fotomodifikatsiya sklery u bolnykh s progressiruyuschei blizorukostyu (predvaritelnoe soobschenie). 2010 [online]. Retrieved from the Internet<URL: http://www.eyepress.ru/article.aspx?7484> (2 pages).

"UV-X: Radiation System for Treatment of Keratokonus," PESCHKE Meditrade GmbH; retrieved from http://www.peschkemed.ch/ on Sep. 27, 2011 (date unknown, prior to Sep. 16, 2008) (1 page).

Vasan S., et al., "An agent cleaving glucose-derived protein crosslinks in vitro and in vivo;" Letters to Nature, vol. 382, pp. 275-278; Jul. 18, 1996 (4 pages).

Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).

Wollensak G., et al., "Collagen Crosslinking of Human and Porcine Sclera," J. Cataract Refract. Surg., vol. 30, Issue 3, pp. 689-695; Mar. 2004 (7 pages).

* cited by examiner

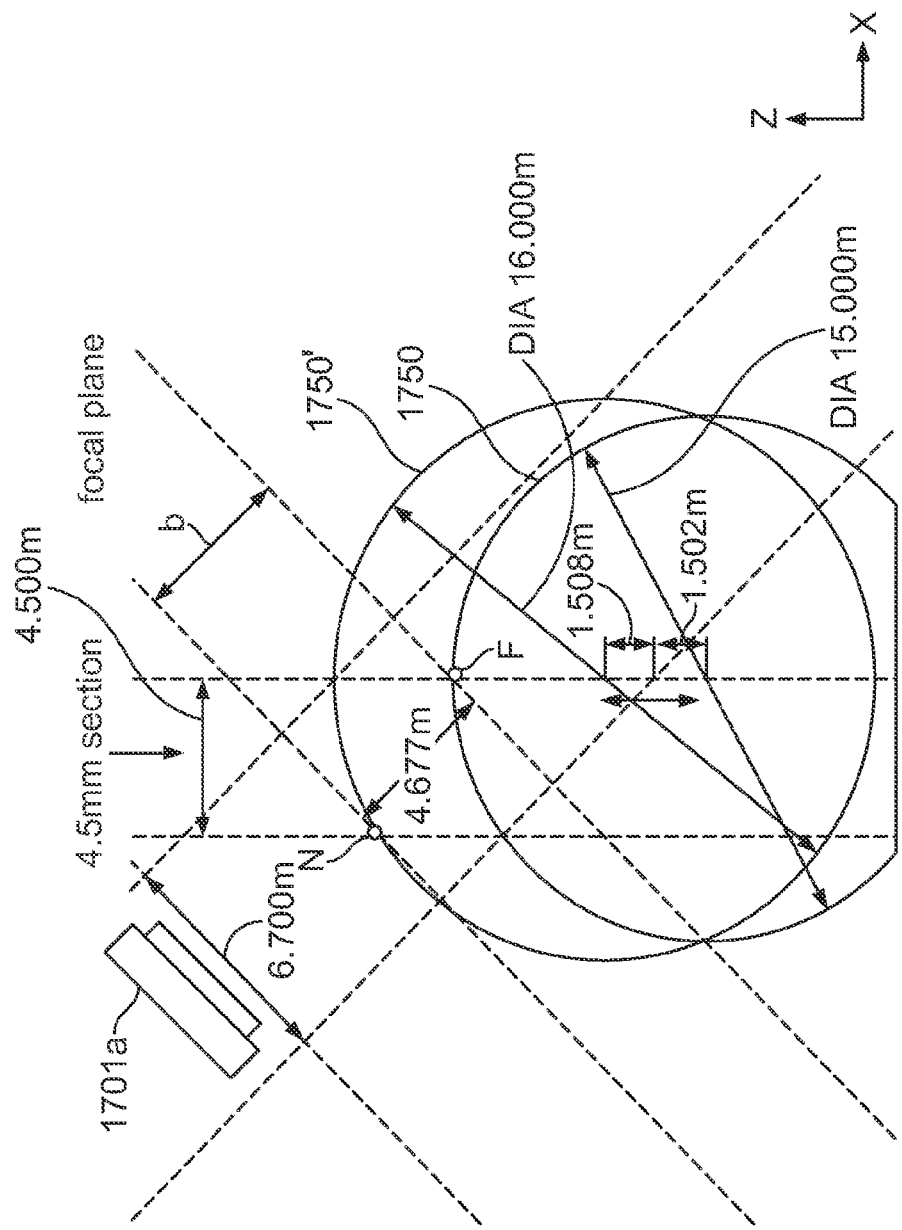

SYSTEMS AND METHODS FOR MONITORING TIME BASED PHOTO ACTIVE AGENT DELIVERY OR PHOTO ACTIVE MARKER PRESENCE

CROSS-REFERENCE TO RELATED APPLICATIONS

This application is a continuation of U.S. patent application Ser. No. 13/488,097, filed Jun. 4, 2012 and issued as U.S. Pat. No. 9,020,580 on Apr. 28, 2015, which claims the benefit of, and priority to, U.S. Provisional Patent Application Ser. No. 61/492,553, filed Jun. 2, 2011; U.S. Provisional Patent Application Ser. No. 61/566,976, filed Dec. 5, 2011; and U.S. Provisional Patent Application Ser. No. 61/594, 796, filed Feb. 3, 2012, the contents of these applications being incorporated entirely herein by reference.

BACKGROUND

Field of the Invention

The invention pertains to systems and methods for monitoring corneal tissue, and more particularly, to systems and methods for monitoring an eye for the presence and distribution of a photo active agent.

Description of Related Art

A variety of eye disorders, such as myopia, keratoconus, and hyperopia, involve abnormal shaping of the cornea. Laser-assisted in-situ keratomileusis (LASIK) is one of a number of corrective procedures that reshape the cornea so that light traveling through the cornea is properly focused onto the retina located in the back of the eye. During LASIK eye surgery, an instrument called a microkeratome is used to cut a thin flap in the cornea. The cornea is then peeled back and the underlying cornea tissue ablated to the desired shape with an excimer laser. After the desired reshaping of the cornea is achieved, the cornea flap is put back in place and the surgery is complete.

In another corrective procedure that reshapes the cornea, thermokeratoplasty provides a noninvasive procedure that applies electrical energy in the microwave or radio frequency (RF) band to the cornea. In particular, the electrical energy raises the corneal temperature until the collagen fibers in the cornea shrink at about 60° C. The onset of shrinkage is rapid, and stresses resulting from this shrinkage reshape the corneal surface. Thus, application of energy according to particular patterns, including, but not limited to, circular or annular patterns, may cause aspects of the cornea to flatten and improve vision in the eye.

The success of procedures, such as LASIK or thermokeratoplasty, in addressing eye disorders, such as myopia, keratoconus, and hyperopia, depends on the stability of the changes in the corneal structure after the procedures have been applied.

SUMMARY

Aspects of the present disclosure provide for monitoring an eye for the presence of a photo-active marker. In one example, a system includes a treatment system that provides a treatment to a corneal tissue. The treatment system includes an applicator that applies a photo-active marker to the corneal tissue. The system also includes an excitation source that directs light to the corneal tissue treated with the photo-active marker. The light causes the photo-active marker to fluoresce. The system additionally includes an image capture system that captures one or more cross-sectional images of the corneal tissue in response to the excitation source directing the light to the corneal tissue. Each cross-sectional image shows the fluorescing photo-active marker along a respective cross-section of the corneal tissue. The system further includes a controller that receives the one or more cross-sectional images and determines information relating to a distribution of the photo-active marker at varying depths across the corneal tissue. The controller provides the distribution information to the treatment system. The treatment system adjusts the treatment of the corneal tissue in response to the distribution information.

In some embodiments, the excitation source directs the light to the corneal tissue as slits of light, and the image capture system includes at least one camera that captures an image of a section of the corneal tissue defined by the slits of light. The at least one camera is offset from an axis defined by the slits of light and is oriented such that an image plane of the at least one camera intersects a focal plane corresponding to the section of the corneal tissue. The image capture system may include two cameras, where the two cameras combine to capture the image of the section of the corneal tissue defined by the slits of light. The excitation source may include a digital micro-mirror device (DMD) to selectively direct the light to the corneal tissue as the slits of light. Alternatively, the excitation source may include a multiple line generator using an optical grating or a scanning mirror system to selectively direct the light to the corneal tissue as the slits of light. The image capture system may further include a lens corresponding to the at least one camera, where the at least one camera captures the image of the section of the corneal tissue via the lens and the image plane of the at least one camera and the focal plane intersect a lens plane of the lens at a common line. An arrangement of the image plane, the lens plane, and the focal plane may minimize a depth of focus. The focal plane may be approximately tangential to a point of a boundary of the corneal tissue at a mid-point of the section being captured by the at least one camera. The excitation source and the image capture system may rotate about the corneal tissue to capture a plurality of cross-sectional images of the corneal tissue.

In other embodiments, the excitation source directs the light to the corneal tissue as slits of light, and the image capture system includes at least one camera configured according to the Scheimpflug principle employing a range of camera angles of approximately 5 to approximately 85 degrees and approximately −5 to approximately 85 degrees.

In yet other embodiments, the controller determines a distribution of the photo-active marker at varying depths across the corneal tissue over a period of time, thereby determining a rate of uptake of the photo-active marker by the corneal tissue.

In further embodiments, the photo-active marker is a cross-linking agent. The treatment system may adjust the treatment of the eye by applying a pattern of ultraviolet light to the corneal tissue to activate cross-linking activity in the corneal tissue. The treatment system may apply the pattern of ultraviolet light via a digital micro-mirror device (DMD). Alternatively, the treatment system may apply the pattern of ultraviolet light via a scanning mirror system.

In additional embodiments, the treatment system adjusts the treatment of the corneal tissue by applying additional photo-active marker to achieve a desired distribution of the photo-active marker. After the application of the additional photo-active marker, the image capture system may capture additional cross-sectional images of the corneal tissue in response to the excitation source directing additional light to the corneal tissue, and the controller determines additional information relating to the distribution of the photo-active marker at varying depths across the corneal tissue to determine whether the desired distribution has been achieved. The treatment system may modify an uptake of the photo-active marker by the corneal tissue. The treatment system may include a permeability regulation system that modifies a permeability of the corneal tissue by applying ultrasound energy or a pattern of radiation to the corneal tissue to increase an uptake of the photo-active marker by the corneal tissue. The permeability regulation system may apply the pattern of radiation via a digital micro-mirror device (DMD). Alternatively, the permeability regulation system may apply the pattern of radiation via a scanning mirror system. The treatment system may apply a diffusion-influencing substance to the corneal tissue.

In other embodiments, the excitation source includes a plurality of slit lamps arranged about the eye tissue, the image capture system capturing the one or more cross-sectional images of the corneal tissue in response to the plurality of slit lamps directing the light to the corneal tissue In yet other embodiments, the excitation source directs the light to the eye tissue as a slit at an incident angle in a range from approximately 20 degrees to approximately 70 degrees relative to the image capture system.

These and other aspects of the present disclosure will become more apparent from the following detailed description of embodiments of the present disclosure when viewed in conjunction with the accompanying drawings.

BRIEF DESCRIPTION OF THE DRAWINGS

FIG. 17C illustrates a focal plane range for the example system of FIG. 17A based on movement of the eye along an axis.

DETAILED DESCRIPTION

Figure 1:
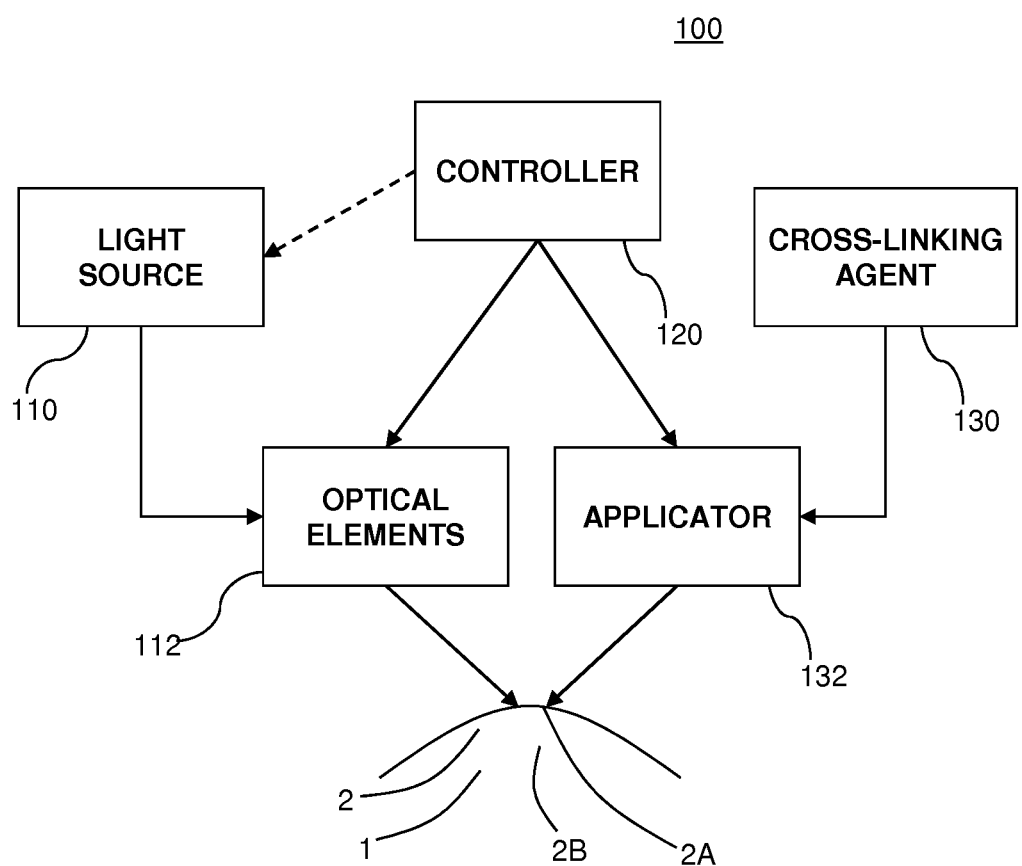
FIG. 1 provides a block diagram of an example delivery system for delivering a cross-linking agent and an activator to a cornea of an eye in order to initiate molecular cross-linking of corneal collagen within the cornea.

FIG. 1 provides a block diagram of an example delivery system 100 for delivering a cross-linking agent 130 and an activator to a cornea 2 of an eye 1 in order to initiate molecular cross-linking of corneal collagen fibrils within the cornea 2. Cross-linking can stabilize corneal tissue and improve its biomechanical strength. The delivery system 100 includes an applicator 132 for applying the cross-linking agent 130 to the cornea 2. The delivery system 100 includes a light source 110 and optical elements 112 for directing light to the cornea 2. The delivery system 100 also includes a controller 120 that is coupled to the applicator 132 and the optical elements 112. The applicator 132 may be an apparatus adapted to apply the cross-linking agent 130 according to particular patterns on the cornea 2 advantageous for causing cross-linking to take place within the corneal tissues. The applicator 132 may apply the cross-linking agent 130 to a corneal surface 2A (e.g., an epithelium), or to other locations on the eye 1. Particularly, the applicator 132 may apply the cross-linking agent 130 to an abrasion or cut of the corneal surface 2A to facilitate the transport or penetration of the cross-linking agent through the cornea 2 to a mid-depth region 2B. The applicator 132 may also be an eye dropper or similar device useful for applying drops of liquid to an eye.

As described below in connection with FIGS. 2A-2B, which describe an exemplary operation of the delivery system 100, the cross-linking agent 130 is applied to the cornea 2 using the applicator 132. Once the cross-linking agent 130 has been applied to the cornea 2, the cross-linking agent 130 is initiated by the light source 110 (i.e. the initiating element) to cause cross-linking agent 130 to absorb enough energy to generate free radicals within the cornea 2. Once generated, the free radicals form covalent bonds between corneal collagen fibrils and thereby cause the corneal collagen fibrils to cross-link and change the structure of the cornea 2. For example, activation of the cross-linking agent 130 with the light source 110 delivered to the cornea 2 through the optical elements 112 may result in cross-linking in the mid-depth region 2B of the cornea 2 and thereby strengthen and stiffen the structure of the cornea 2.

Although eye therapy treatments may initially achieve desired reshaping of the cornea 2, the desired effects of reshaping the cornea 2 may be mitigated or reversed at least partially if the collagen fibrils within the cornea 2 continue to change after the desired reshaping has been achieved. Indeed, complications may result from further changes to the cornea 2 after treatment. For example, a complication known as post-LASIK ectasia may occur due to the permanent thinning and weakening of the cornea 2 caused by LASIK surgery. In post-LASIK ectasia, the cornea 2 experiences progressive steepening (bulging).

Aspects of the present disclosure provide approaches for initiating molecular cross-linking of corneal collagen to stabilize corneal tissue and improve its biomechanical strength. For example, embodiments may provide devices and approaches for preserving the desired corneal structure and shape that result from an eye therapy treatment, such as LASIK surgery or thermokeratoplasty. In addition, aspects of the present disclosure may provide devices and approaches for monitoring the shape, molecular cross-linking, and biomechanical strength of the corneal tissue and providing feedback to a system for providing iterative initiations of cross-linking of the corneal collagen. As described herein, the devices and approaches disclosed herein may be used to preserve desired shape or structural changes following an eye therapy treatment by stabilizing the corneal tissue of the cornea 2. The devices and approaches disclosed herein may also be used to enhance the strength or biomechanical structural integrity of the corneal tissue apart from any eye therapy treatment.

Therefore, aspects of the present disclosure provide devices and approaches for preserving the desired corneal structure and shape that result from an eye treatment, such as LASIK surgery or thermokeratoplasty. In particular, embodiments may provide approaches for initiating molecular cross-linking of the corneal collagen to stabilize the corneal tissue and improve its biomechanical strength and stiffness after the desired shape change has been achieved. In addition, embodiments may provide devices and approaches for monitoring cross-linking in the corneal collagen and the resulting changes in biomechanical strength to provide a feedback to a system for inducing cross-linking in corneal tissue.

Some approaches initiate molecular cross-linking in a treatment zone of the cornea 2 where structural changes have been induced by, for example, LASIK surgery or thermokeratoplasty. However, it has been discovered that initiating cross-linking directly in this treatment zone may result in undesired haze formation. Accordingly, aspects of the present disclosure also provide alternative techniques for initiating cross-linking to minimize haze formation. In particular, the structural changes in the cornea 2 are stabilized by initiating cross-linking in selected areas of corneal collagen outside of the treatment zone. This cross-linking strengthens corneal tissue neighboring the treatment zone to support and stabilize the actual structural changes within the treatment zone.

With reference to FIG. 1, the optical elements 112 may include one or more mirrors or lenses for directing and focusing the light emitted by the light source 110 to a particular pattern on the cornea 2 suitable for activating the cross-linking agent 130. The light source 110 may be an ultraviolet light source, and the light directed to the cornea 2 through the optical elements 112 may be an activator of the cross-linking agent 130. The light source 110 may also alternatively or additionally emit photons with greater or lesser energy levels than ultraviolet light photons. The delivery system 100 also includes a controller 120 for controlling the operation of the optical elements 112 or the applicator 132, or both. By controlling aspects of the operation of the optical elements 112 and the applicator 132, the controller 120 can control the regions of the cornea 2 that receive the cross-linking agent 130 and that are exposed to the light source 110. By controlling the regions of the cornea 2 that receive the cross-linking agent 130 and the light source 110, the controller 120 can control the particular regions of the cornea 2 that are strengthened and stabilized through cross-linking of the corneal collagen fibrils. In an implementation, the cross-linking agent 130 can be applied generally to the eye 1, without regard to a particular region of the cornea 2 requiring strengthening, but the light source 110 can be directed to a particular region of the cornea 2 requiring strengthening, and thereby control the region of the cornea 2 wherein cross-linking is initiated by controlling the regions of the cornea 2 that are exposed to the light source 110.

The optical elements 112 can be used to focus the light emitted by the light source 110 to a particular focal plane within the cornea 2, such as a focal plane that includes the mid-depth region 2B. In addition, according to particular embodiments, the optical elements 112 may include one or more beam splitters for dividing a beam of light emitted by the light source 110, and may include one or more heat sinks for absorbing light emitted by the light source 110. The optical elements 112 may further include filters for partially blocking wavelengths of light emitted by the light source 110 and for advantageously selecting particular wavelengths of light to be directed to the cornea 2 for activating the cross-linking agent 130. The controller 120 can also be adapted to control the light source 110 by, for example, toggling a power switch of the light source 110.

In an implementation, the controller 120 may include hardware and/or software elements, and may be a computer. The controller 120 may include a processor, a memory storage, a microcontroller, digital logic elements, software running on a computer processor, or any combination thereof. In an alternative implementation of the delivery system 100 shown in FIG. 1, the controller 120 may be replaced by two or more separate controllers or processors. For example, one controller may be used to control the operation of the applicator 132, and thereby control the precise rate and location of the application of the cross-linking agent 130 to the cornea 2. Another controller may be used to control the operation of the optical elements 112, and thereby control with precision the delivery of the light source 110 (i.e. the initiating element) to the cornea 2 by controlling any combination of: wavelength(s), spectral bandwidth(s), intensity(s), power(s), location(s), depth(s) of penetration, and duration(s) of treatment. In addition, the function of the controller 120 can be partially or wholly replaced by a manual operation. For example, the applicator 132 can be manually operated to deliver the cross-linking agent 130 to the cornea 2 without the assistance of the controller 120. In addition, the controller 120 can operate the applicator 132 and the optical elements 112 according to inputs dynamically supplied by an operator of the delivery system 100 in real time, or can operate according to a pre-programmed sequence or routine.

Figure 2A:
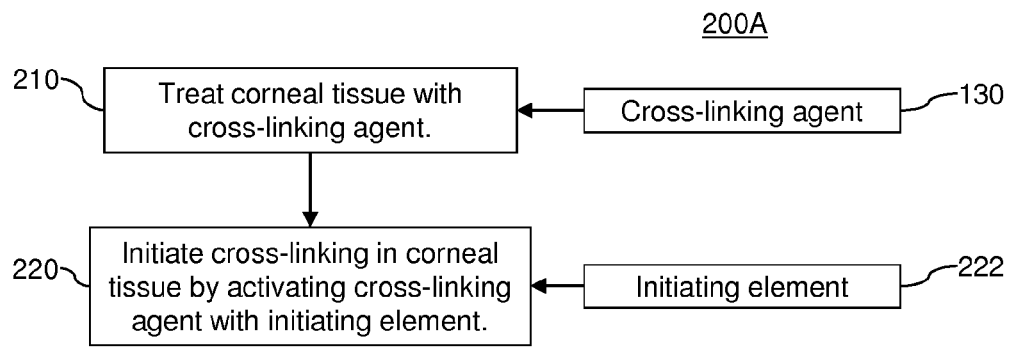
FIG. 2A provides a flowchart showing an example embodiment according to aspects of the present disclosure for activating cross-linking within cornea tissue using a cross-linking agent and an initiating element.

Referring to FIG. 2A, an example embodiment 200A according to aspects of the present disclosure is illustrated. Specifically, in step 210, the corneal tissue is treated with the cross-linking agent 130. Step 210 may occur, for example, after a treatment is applied to generate structural changes in the cornea and produce a desired shape change. Alternatively, step 210 may occur, for example, after it has been determined that the corneal tissue requires stabilization or strengthening. The cross-linking agent 130 is then activated in step 220 with an initiating element 222. In an example configuration, the initiating element 222 may be the light source 110 shown in FIG. 1. Activation of the cross-linking agent 130, for example, may be triggered thermally by the application of microwaves or light.

Figure 2B:
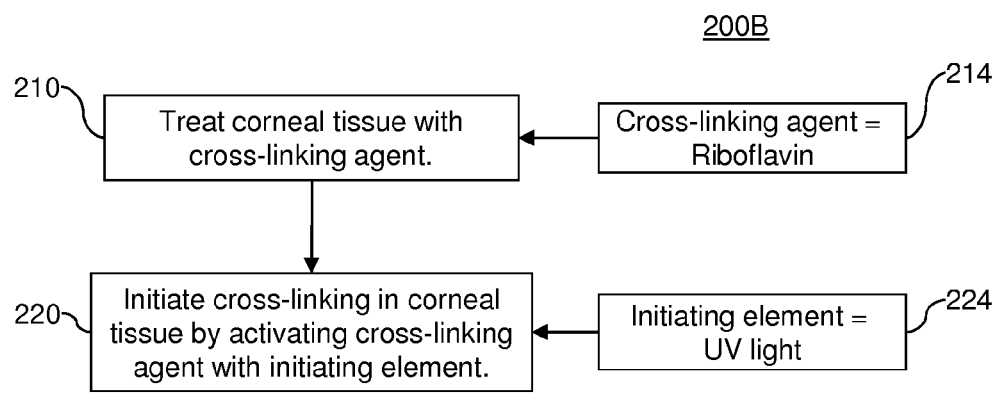
FIG. 2B provides a flowchart similar to FIG. 2A where Riboflavin may be applied topically as the cross-linking agent and UV light may be applied as the initiating element.

As the example embodiment 200B of FIG. 2B shows further, Riboflavin may be applied topically as a cross-linking agent 214 to the corneal tissue in step 210. As also shown in FIG. 2B, ultraviolet (UV) light may be applied as an initiating element 224 in step 220 to initiate cross-linking in the corneal areas treated with Riboflavin. Specifically, the UV light initiates cross-linking activity by causing the applied Riboflavin to generate reactive Riboflavin radicals and reactive oxygen radicals in the corneal tissue. The Riboflavin thus acts as a sensitizer to radical Riboflavin and to convert molecular oxygen to singlet oxygen, which in turn causes cross-linking within the corneal tissue.

According to one approach, the Riboflavin may be applied topically to the corneal surface, and transepithelial delivery allows the Riboflavin to be applied to the corneal stroma. In general, the application of the cross-linking agent sufficiently introduces Riboflavin to mid-depth regions of the corneal tissue where stronger and more stable structure is desired.

Where the initiating element is UV light, the UV light may be generally applied to the corneal surface 2A (e.g. the epithelium) of the cornea 2 to activate cross-linking. However, regions of the cornea 2 requiring stabilization may extend from the corneal surface 2A to a mid-depth region 2B in the corneal stroma 2C. Generally applying UV light to the corneal surface 2A may not allow sufficient penetration of the UV light to activate necessary cross-linking at a mid-depth region 2B of the cornea 2. Accordingly, aspects of the present disclosure provide a delivery system that accurately and precisely delivers UV light to the mid-depth region 2B where stronger and more stable corneal structure is required. In particular, treatment may generate desired changes in corneal structure at the mid-depth region 2B.

Figure 3:
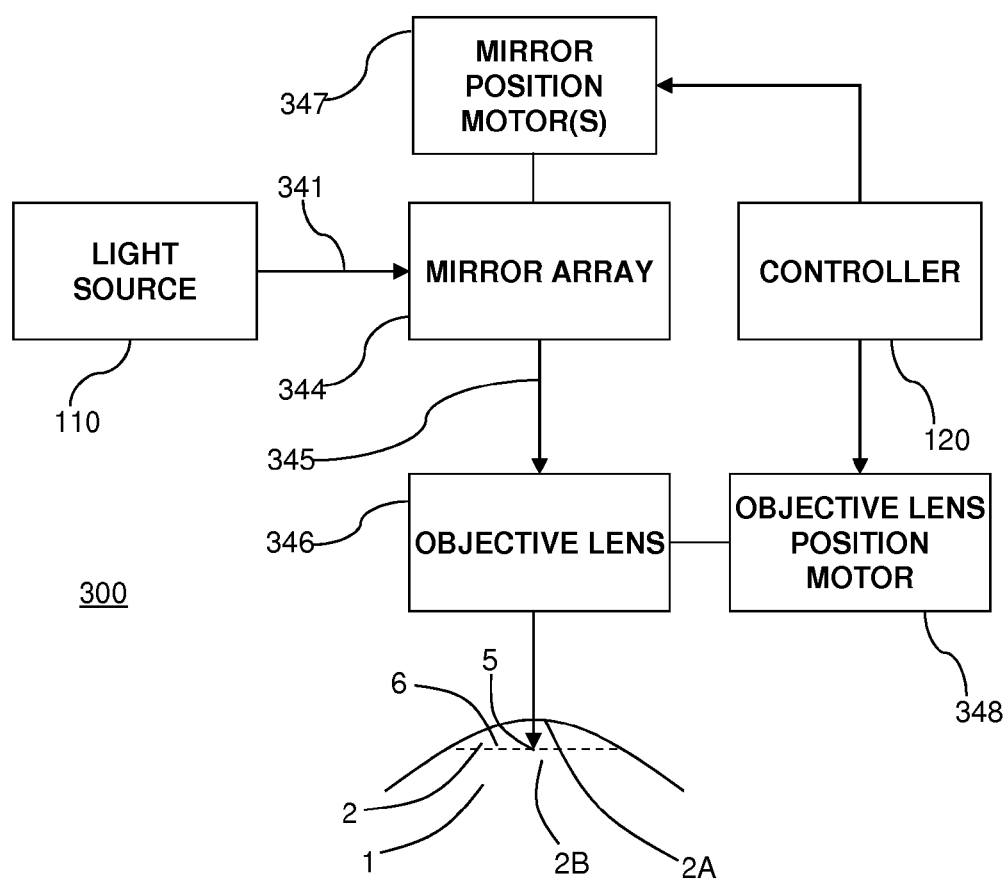
FIG. 3 provides an example delivery system adapted as a laser scanning device for delivering light to the cornea employing laser scanning technology.

FIG. 3 provides an example delivery system adapted as a laser scanning device 300 for delivering light to the cornea 2 employing laser scanning technology. The laser scanning device 300 has the light source 110 for delivering a laser beam through an objective lens 346 into a small focal volume within the cornea 2. The laser scanning device 300 also includes the controller 120 for controlling the intensity profile of the light delivered to the cornea 2 using a mirror array 344 and for controlling the focal plane of the objective lens 346. The light source 110 can be an ultraviolet (UV) light source that emits a UV laser. A beam of light 341 is emitted from the light source 110 (e.g., UV laser) and passes to the mirror array 344. Within the mirror array 344, the beam of light 341 from the light source 110 is scanned over multiple mirrors adapted in an array. The beam of light 341 can be scanned over the mirrors in the mirror array 344 using, for example, one or more adjustable mirrors to direct the beam of light 341 to point at each mirror in turn. The beam of light 341 can be scanned over each mirror one at a time. Alternately, the beam of light 341 can be split into one or more additional beams of light using, for example, a beam splitter, and the resultant multiple beams of light can then be simultaneously scanned over multiple mirrors in the mirror array 344.

By rapidly scanning the beam of light 341 over the mirrors in the mirror array 344, the mirror array 344 outputs a light pattern 345, which has a two dimensional intensity pattern. The two dimensional intensity pattern of the light pattern 345 is generated by the mirror array 344 according to, for example, the length of time that the beam of light 341 is scanned over each mirror in the mirror array 344. In particular, the light pattern 345 can be considered a pixilated intensity pattern with each pixel represented by a mirror in the mirror array 344 and the intensity of the light in each pixel of the light pattern 345 proportionate to the length of time the beam of light 341 scans over the mirror in the mirror array 344 corresponding to each pixel. In an implementation where the beam of light 341 scans over each mirror in the mirror array 344 in turn to create the light pattern 345, the light pattern 345 is properly considered a time-averaged light pattern, as the output of the light pattern 345 at any one particular instant in time may constitute light from as few as a single pixel in the pixelated light pattern 345. In an implementation, the laser scanning technology of the delivery system 300 may be similar to the technology utilized by Digital Light Processing™ (DLP®) display technologies.

The mirror array 344 can include an array of small oscillating mirrors, controlled by mirror position motors 347. The mirror position motors 347 can be servo motors for causing the mirrors in the mirror array 344 to rotate so as to alternately reflect the beam of light 341 from the light source 340 toward the cornea 2 (e.g., alternately directed to be part of the pattern of light delivered to the cornea 2 via one or more optical elements). The controller 120 can control the light pattern 345 generated in the mirror array 344 using the mirror position motors 347. In addition, the controller 120 can control the depth within the cornea 2 that the light pattern 345 is focused to by controlling the location of the focal depth of the objective lens 346 relative to the corneal surface 2A. For example, the controller 120 can utilize an objective lens position motor 348 to raise and/or lower the objective lens 346 in order to adjust the focal plane 6 of the light pattern 345 emitted from the mirror array 344. By adjusting the focal plane 6 of the light pattern 345 using the objective lens motor 348, and controlling the two-dimensional intensity profile of the light pattern 345 using the mirror position motors 347, the controller 120 is adapted to control the delivery of the light source 110 to the cornea 2 in three dimensions. The three-dimensional pattern is generated by delivering the UV light to selected regions 5 on successive planes (parallel to the focal plane 6), which extend from the corneal surface 2A to the mid-depth region 2B within the corneal stroma. The cross-linking agent 130 introduced into the selected regions 5 is then activated as described above.

By scanning over selected regions 5 of a plane 6 at a particular depth within the cornea 2, the controller 120 can control the activation of the cross-linking agent 130 within the cornea 2 according to a three dimensional profile. In particular, the controller 120 can utilize the laser scanning technology of the laser scanning device 300 to strengthen and stiffen the corneal tissues by activating cross-linking in a three-dimensional pattern within the cornea 2. In an implementation, the objective lens 346 can be replaced by an optical train consisting of mirrors and/or lenses to properly focus the light pattern 345 emitted from the mirror array 344. Additionally, the objective lens motor 348 can be replaced by a motorized device for adjusting the position of the eye 1 relative to the objective lens 346, which can be fixed in space. For example, a chair or lift that makes fine motor step adjustments and adapted to hold a patient during eye treatment can be utilized to adjust the position of the eye 1 relative to the objective lens 346.

Advantageously, the use of laser scanning technologies allows cross-linking to be activated beyond the corneal surface 2A of the cornea 2, at depths where stronger and more stable corneal structure is desired, for example, where structural changes have been generated by an eye therapy treatment. In other words, the application of the initiating element (i.e., the light source 110) is applied precisely according to a selected three-dimensional pattern and is not limited to a two-dimensional area at the corneal surface 2A of the cornea 2.

Although the embodiments described herein may initiate cross-linking in the cornea according to an annular pattern defined, for example, by a thermokeratoplasty applicator, the initiation pattern in other embodiments is not limited to a particular shape. Indeed, energy may be applied to the cornea in non-annular patterns, so cross-linking may be initiated in areas of the cornea that correspond to the resulting non-annular changes in corneal structure. Examples of the non-annular shapes by which energy may be applied to the cornea are described in U.S. patent Ser. No. 12/113,672, filed on May 1, 2008, the contents of which are entirely incorporated herein by reference.

Some embodiments may employ Digital Micromirror Device (DMD) technology to modulate the application of initiating light, e.g., UV light, spatially as well as temporally. Using DMD technology, a controlled light source is selectively reflected to provide the initiating light in a precise spatial pattern that is created by microscopically small mirrors laid out in a matrix on a semiconductor chip, known as a DMD. Each mirror represents one or more pixels in the pattern of reflected light. The power and duration at which the light is reflected to provide the pixelated intensity pattern is determined as described elsewhere. Alternatively, some embodiments may employ a scanning mirror system to apply the patterns of initiating light.

Embodiments may also employ aspects of multiphoton excitation microscopy. In particular, rather than delivering a single photon of a particular wavelength to the cornea 2, the delivery system (e.g., 100 in FIG. 1) delivers multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than shorter wavelength light. For example, in some embodiments, two photons may be employed, where each photon carries approximately half the energy necessary to excite the molecules in the cross-linking agent 130 that generate radicals and reactive oxygen radicals. When a cross-linking agent molecule simultaneously absorbs both photons, it absorbs enough energy to generate reactive Riboflavin radicals and/or reactive oxygen radicals in the corneal tissue, and thereby initiate cross-linking. Embodiments may also utilize lower energy photons such that a cross-linking agent molecule must simultaneously absorb, for example, three, four, or five, photons to generate reactive Riboflavin radicals and/or reactive oxygen radicals. The probability of the near-simultaneous absorption of multiple photons is low, so a high flux of excitation photons may be required, and the high flux may be delivered through a femtosecond laser. Because multiple photons are absorbed for activation of the cross-linking agent molecule, the probability for activation increases with intensity. Therefore, more activation occurs where the delivery of light from the light source 110 is tightly focused compared to where it is more diffuse. The light source 110 may deliver a laser beam to the cornea 2. Effectively, activation of the cross-linking agent 330 is restricted to the smaller focal volume where the light source 310 is delivered to the cornea 2 with a high flux. This localization advantageously allows for more precise control over where cross-linking is activated within the cornea 2.

Referring again to FIG. 1, embodiments employing multiphoton excitation microscopy can also optionally employ multiple beams of light simultaneously applied to the cornea 2 by the light source 110. For example, a first and a second beam of light can each be directed from the optical elements 112 to an overlapping region of the cornea 2. The region of intersection of the two beams of light can be a volume in the cornea 2 where cross-linking is desired to occur. Multiple beams of light can be delivered to the cornea 2 using aspects of the optical elements 112 to split a beam of light emitted from the light source 310 and direct the resulting multiple beams of light to an overlapping region of the cornea 2. In addition, embodiments employing multiphoton excitation microscopy can employ multiple light sources, each emitting a beam of light that is directed to the cornea 2, such that the multiple resulting beams of light overlap or intersect in a volume of the cornea 2 where cross-linking is desired to occur. The region of intersection may be, for example, in the mid-depth region 2B of the cornea 2, and may be below the corneal surface 2A. Aspects of the present disclosure employing overlapping beams of light to achieve multiphoton microscopy may provide an additional approach to controlling the activation of the cross-linking agent 130 according to a three-dimensional profile within the cornea 2.

Aspects of the present disclosure can be employed to reduce the amount of time required to achieve the desired cross-linking. For example, parameters for delivery and activation of the cross-linking agent 130 can be adjusted to reduce the amount of time required to achieve cross-linking. In an example implementation, the time can be reduced from minutes to seconds. While some configurations may apply the initiating element (i.e., the light source 110) at a flux dose of 5 J/cm$^2$, aspects of the present disclosure allow larger doses of the initiating element, e.g., multiples of 5 J/cm$^2$, to be applied to reduce the time required to achieve the desired cross-linking. Highly accelerated cross-linking is particularly possible when using laser scanning technologies (such as in the delivery system 300 provided in FIG. 3) in combination with a feedback system 400 as shown in FIG. 4, such as a rapid video eye-tracking system, described below.

To decrease the treatment time, and advantageously generate stronger cross-linking within the cornea 2, the initiating element (e.g., the light source 110 shown in FIG. 1) may be applied with a power between 30 mW and 1 W. The total dose of energy absorbed in the cornea 2 can be described as an effective dose, which is an amount of energy absorbed through a region of the corneal surface 2A. For example the effective dose for a region of the cornea 2 can be, for example, 5 J/cm$^2$, or as high as 20 J/cm$^2$ or 30 J/cm$^2$. The effective dose delivering the energy flux just described can be delivered from a single application of energy, or from repeated applications of energy. In an example implementation where repeated applications of energy are employed to deliver an effective dose to a region of the cornea 2, each subsequent application of energy can be identical, or can be different according to information provided by the feedback system 400.

Treatment of the cornea 2 by activating cross-linking produces structural changes to the corneal stroma. In general, the opto-mechanical properties of the cornea 2 changes under stress. Such changes include: straightening out the waviness of the collagen fibrils; slippage and rotation of individual lamellae; and breakdown of aggregated molecular superstructures into smaller units. In such cases, the application of the cross-linking agent 130 introduces sufficient amounts of cross-linking agent 130 to mid-depth regions 2B of the corneal tissue where stronger and more stable structure is desired. The cross-linking agent 130 may be applied directly to corneal tissue that have received an eye therapy treatment and/or in areas around the treated tissue.

Figure 4:
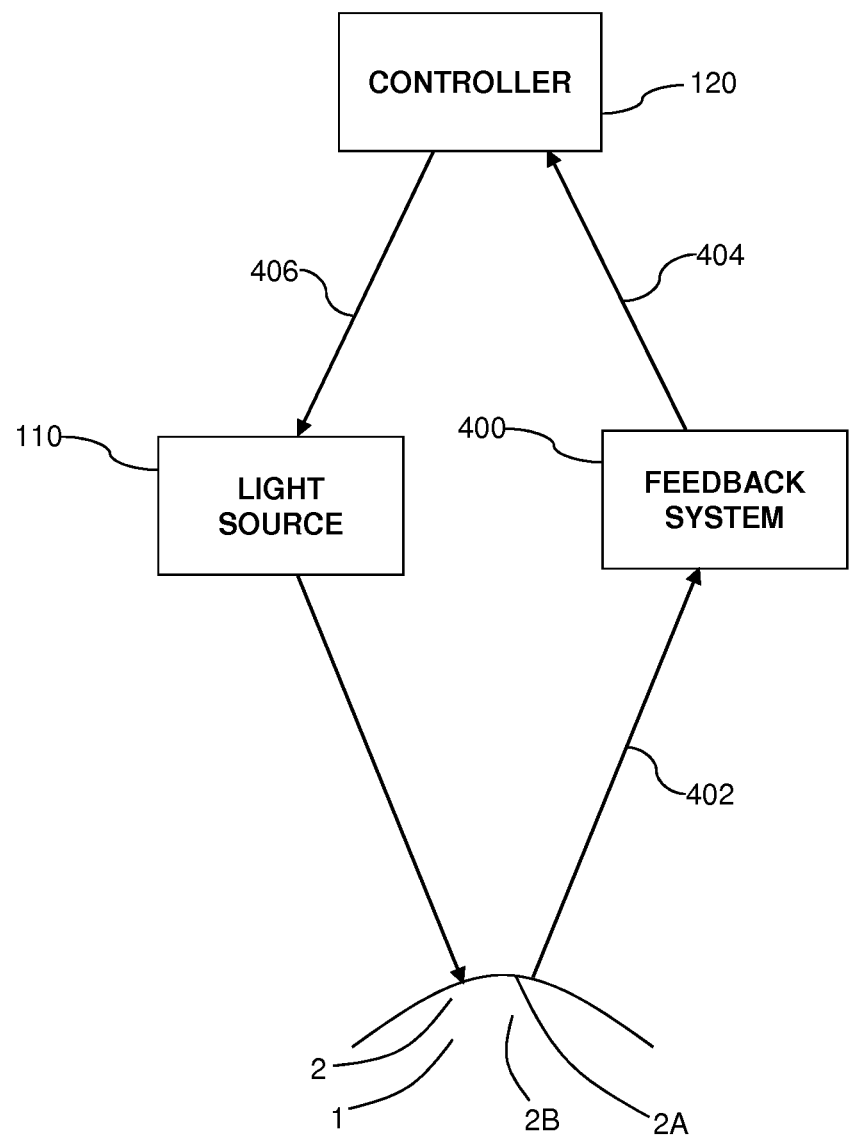
FIG. 4 illustrates a delivery system incorporating a feedback system.

To enhance safety and efficacy of the application and the activation of the cross-linking agent, aspects of the present disclosure provide techniques for real time monitoring of the changes to the collagen fibrils with a feedback system 400 shown in FIG. 4. These techniques may be employed to confirm whether appropriate doses of the cross-linking agent 130 have been applied during treatment and/or to determine whether the cross-linking agent 130 has been sufficiently activated by the initiating element (e.g., the light source 110). General studies relating to dosage may also apply these monitoring techniques.

Moreover, real time monitoring with the feedback system 400 may be employed to identify when further application of the initiating element (e.g., the light source 110) yields no additional cross-linking. Where the initiating element is UV light, determining an end point for the application of the initiating element protects the corneal tissue from unnecessary exposure to UV light. Accordingly, the safety of the cross-linking treatment is enhanced. The controller 120 for the cross-linking delivery system can automatically cease further application of UV light when the real time monitoring from the feedback system 400 determines that no additional cross-linking is occurring.

FIG. 4 illustrates a delivery system incorporating the feedback system 400. The feedback system 400 is adapted to gather measurements 402 from the eye 1, and pass feedback information 404 to the controller 120. The measurements 402 can be indicative of the progress of strengthening and stabilizing the corneal tissue. The measurements 402 can also provide position information regarding the location of the eye and can detect movement of the cornea 2, and particularly the regions of the corneal tissue requiring stabilization. The feedback information 404 is based on the measurements 402 and provides input to the controller 120. The controller 120 then analyzes the feedback information 404 to determine how to adjust the application of the initiating element, e.g., the light source 110, and sends command signals 406 to the light source 110 accordingly. Furthermore, the delivery system 100 shown in FIG. 1 can be adapted to incorporate the feedback system 100 and can adjust any combination of the optical elements 112, the applicator 132, or the light source 110 in order to control the activation of the cross-linking agent 130 within the cornea 2 based on the feedback information 404 received from the feedback system 400. As will be described further below, the feedback system 400 can be a measurement system for determining a distribution of a fluorescent marker in the eye 1.

Figure 5A:
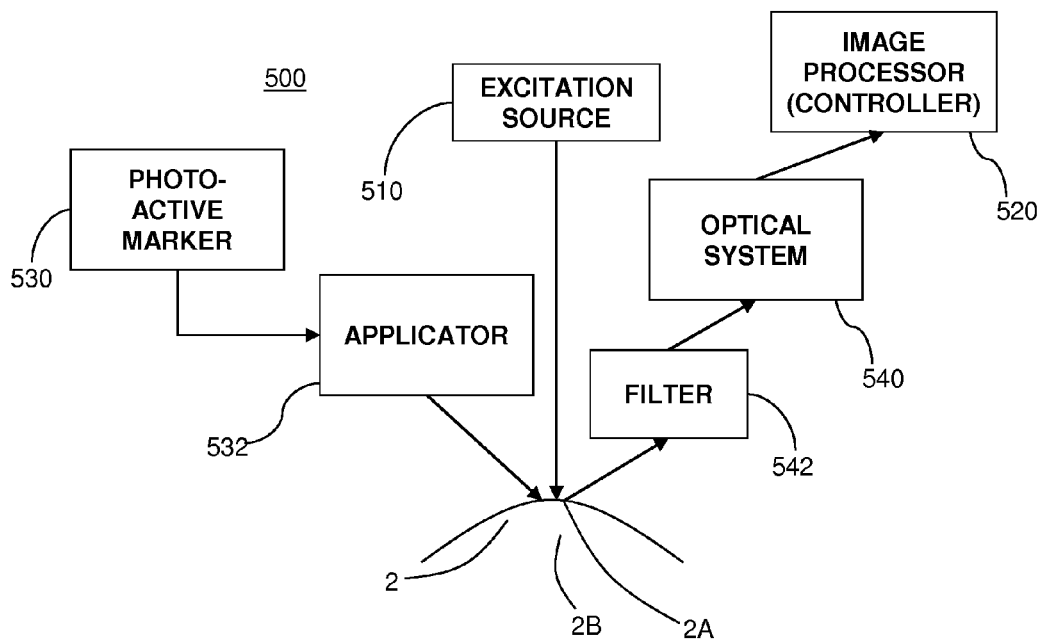
FIG. 5A illustrates an example fluorescence dosimetry system.

FIG. 5A illustrates an example fluorescence dosimetry system 500. The fluorescence dosimetry system 500 includes an applicator 532 for applying a photo-active marker 530 to an eye 1, having a cornea 2. The applicator 532 can be similar to the applicator 132 described in connection with FIG. 1, and can be a device suitable for instillation of the photo-active marker 530 to the eye 1. For example, the applicator 532 can be an eye dropper or similar device that applies the photo-active marker 530 to the corneal surface 2A in drops. The fluorescence dosimetry system 500 also includes an excitation source 510, which can be a light source such as a UV light source. The excitation source 510 is generally conveyed to the eye 1 via optical elements to advantageously apply the excitation source 510 according to a desired pattern. The optical elements can include, for example, mirrors, lenses, apertures, filters, and the like. In an implementation the excitation source can be a light source in the UVA wavelength range, such as 365 nm to 370 nm. The excitation source 510 is advantageously selected such that the light and/or energy applied to the eye 1 is suitable for exciting the photo-active marker 530 to cause the photo-active marker 530 to fluoresce within the tissue of the eye 1. Depending on the particular photo-active marker utilized in a particular implementation of the fluorescence dosimetry system 500, the excitation source 510 may be suitably chosen so as to complement the particular photo-active marker employed.

The fluorescence dosimetry system 500 also includes an optical system 540 for capturing one or more images of the eye 1 while the photo-active marker 1 is excited to fluoresce. The presence of light at the characteristic fluorescence emission frequencies of the photo-active marker 530 in the images captured via the optical system 540 is therefore indicative of the presence and/or distribution of the photo-active marker 530 in the eye 1. As will be further described below, the optical system 540 may be implemented as a Scheimpflug single or dual imaging and/or rotating optical system or as one or more slit lamps to illuminate cross-sectional portions of the cornea 2. In such an implementation, each image provides an indication of the presence of the photo-active marker 530 along a particular cross-section of the cornea 2. An image processor 520 is also provided to analyze the images acquired via the optical system 540 and determine, based on the series of images information regarding the presence and/or distribution of the photo-active marker 530 in the eye 1. The fluorescence dosimetry system 500 can also incorporate a filter 542 to advantageously block wavelengths of light corresponding to the excitation source 510. By selecting the filter 542 such that the light applied to the eye 1 via the excitation source 510 (i.e., the exciting light) is blocked while wavelengths corresponding to the excitation emission wavelengths are allowed to pass (i.e., the emissive light), the image(s) captured by the optical system 540 indicate the emissive light. For example, the filter 542 can be configured to transmit the exciting light while substantially blocking the emissive light (from the distributed photo-active marker 530). Thus, the filter 542 can improve the signal to noise of the fluorescence dosimetry system 500 by isolating the light emitted from the photo-active marker 530 from the light applied by the excitation source 510.

Figure 5B:
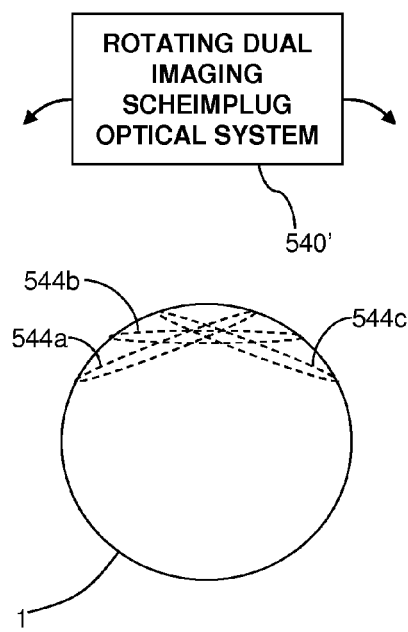
FIG. 5B provides a schematic view of example cross-sectional images of an eye that can be captured via a rotating dual imaging Scheimpflug optical system.

FIG. 5B provides a schematic view of example cross-sectional images of an eye 1 that can be captured via a rotating dual imaging Scheimpflug optical system 540'. The rotating dual Scheimpflug optical system 540' includes two cameras and light applied to the eye 1 via a narrow slit ("aperture"). As is commonly understood in a Scheimpflug system, the two cameras are oriented such that their respective image planes intersect with the object plane of the features of the eye 1 being imaged. A dual Scheimpflug system 540' allows for an enhanced depth of focus relative to an imaging system oriented with optical and image planes parallel. The dual Scheimpflug system 540' is utilized to extract a series of planes of the cornea 2, such as the planes 544a, 544b, 544c schematically illustrated in FIG. 5B. In an implementation, the dual Scheimpflug system 540' can rotate about an axis of the eye 1 such that a series of images for cross-sectional portions of the eye 1 are captured as the dual Scheimpflug system 540' travels through 180 degrees. Properly filtered, such as with the filter 542, the cross-sectional images extracted by the rotating dual imaging Scheimpflug optical system 540' are each indicative of a concentration of the photo-active marker 530 in the eye 1 along each imaged cross-section (e.g., the cross sections 544a, 544b, 544c).

While the dual imaging Scheimpflug optical system 540' is provided for example purposes, it is acknowledged that implementations of the present disclosure are not limited to dual imaging Scheimpflug systems, and apply to a variety of optical systems suitable for capturing intensity profiles indicative of intensities at a variety of depths within an eye. For example, single imaging Scheimpflug systems, slit lamp systems (as described further below), optical coherence tomography (OCT) systems, and optically similar systems adapted to capture images of cross-sectional portion of the eye 1 can be utilized as the optical system 540 illustrated in FIG. 5A. Furthermore, aspects of the present disclosure apply to optical systems that are adapted to capture a single cross-sectional image of the eye 1.

Figure 6:
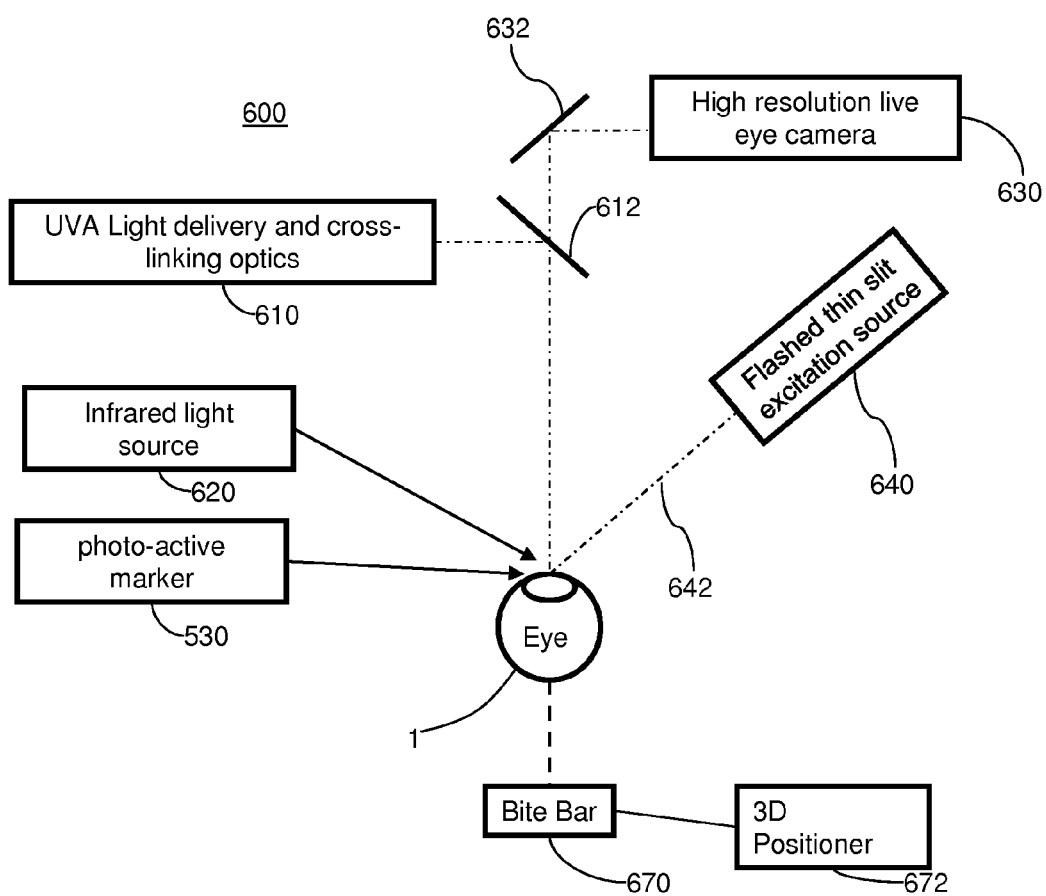
FIG. 6 provides another exemplary implementation of a fluorescence dosimetry system utilizing a thin slit excitation source.

FIG. 6 provides another exemplary implementation of a fluorescence dosimetry system 600 utilizing a thin slit excitation source 640. The system 600 includes a high resolution live eye camera 630 that is oriented to capture images of the eye 1 via the mirror 632. The thin slit excitation source 640 is oriented to convey the excitation light 642 to the eye 1 at a high incident angle. For example, the excitation light 642 can be delivered to the eye 1 at an incident angle in a range of approximately 20 degrees to approximately 70 degrees, e.g., a 45 degree incident angle.

The excitation source 640 can be a light source suitable for generating the excitation light 642 that excites the photo-active marker 530 and can be conveyed to the eye 1 in a beam formed as a narrow slit so as to illuminate a cross-sectional portion of the eye 1. The system 600 also includes UVA light delivery and cross-linking optics 610 which directs UVA light to the eye 1 via a dichroic mirror 612. The dichroic mirror 612 advantageously reflects light corresponding to the excitation light 642, but allows light corresponding to the fluorescence emission of the photo-active marker 530 to pass. For example, where the excitation light 642 is 365 nm to 370 nm UVA light, the dichroic mirror 612 can reflect light with those wavelengths, while having a long pass characteristic above 430 nm. Implementations of the present disclosure may optionally utilize one or more filters to provide similar spectral characteristics to the dichroic mirror 612. The camera 630 can be utilized to detect images of the eye 1 while the eye 1 is illuminated with the excitation light 642. Because the excitation light 642 is blocked by the dichroic mirror 612, the images detected by the camera 630 are due to the fluorescence of the photo-active marker 530 in the cross-sectional portion of the eye 1 illuminated by the thin slit excitation source 640. For example, the camera 630 can periodically capture one or more full resolution image(s) indicative of the distribution of the photo-active marker 530 (e.g., fluorescent dosimetry images), while providing targeting ("positioning") information from low resolution images captured in between the full resolution dosimetry images. In addition, the thin slit excitation source 640 can be flashed to only periodically illuminate the eye 1 with the excitation light 642 during and/or prior to intervals when the camera 630 is capturing the fluorescent dosimetry images.

The system 600 optionally further provides for the position of the eye 1 to be fixed via a bite bar 670. The bite bar can be a deformable material for a patient to bite down on with their jaw to thereby fix the position of a patient's head and prevent the patient's head from moving relative to the bite bar 670. The bite bar 670 can be coupled to a 3d positioner 672 that incorporates motors and the like to manipulate the bite bar 670 in three dimensions to correct and/or compensate the position of the eye 1 during a cross-linking operation according to the monitoring ("targeting") information provided via the camera 630. Thus, the camera 630 can be utilized to both provide targeting ("positioning") information and provide images indicative of the distribution of the photo-active marker 530. While the camera 630 is providing targeting information, the resolution of the camera 630 can be sub-sampled to allow for more rapid data collection and analysis in order to actively compensate for movement of the eye 1 during cross-linking activation. Implementations including active targeting and positioning feedback may allow for the patient to receive cross-linking therapy while sitting upright rather than lying down. Cross-linking can be done with a patient lying on their back during a surgical procedure. With the patient lying on their back, gravity directs the applied drops (e.g., drops of cross-linking agent, photo-active marker, etc.) to the eye 1 and to increase uniformity of their application.

Implementations of the present disclosure also apply to systems lacking the bite bar 670. The system 600 also includes an infrared light source 620, which is oriented to illuminate the eye 1 with infrared radiation. Infrared radiation from the eye 1 can then be detected by the camera 630 to monitor the position of the eye 1 during a cross-linking operation (e.g., provide targeting and active tracking). The UVA light delivery system 610 can then be adjusted in real time according to the dynamically monitored position (via the camera 630 and associated image processing system(s)) such that the delivered light is directed to the eye in a substantially constant and location, with respect to the eye 1, even as the location of the eye 1 changes. For example, one or more mirrors and/or lenses associated with the UVA delivery system 610 can be dynamically adjusted according to the positioning information such that the delivered light tracks the position of the eye 1. The infrared radiation advantageously allows for illumination of the eye 1 (to provide positioning feedback) without distracting the patient, because the infrared radiation is not perceived by the patient. The infrared light source 620 and the camera 630 can also be utilized during a diagnostic interval to topographically characterize the cornea 2 prior to initiation of cross-linking. For example, the camera 630 can be utilized in combination with a multiple slit lamp configuration such as the configuration illustrated in FIG. 7A.

Figures 7A, 7B:
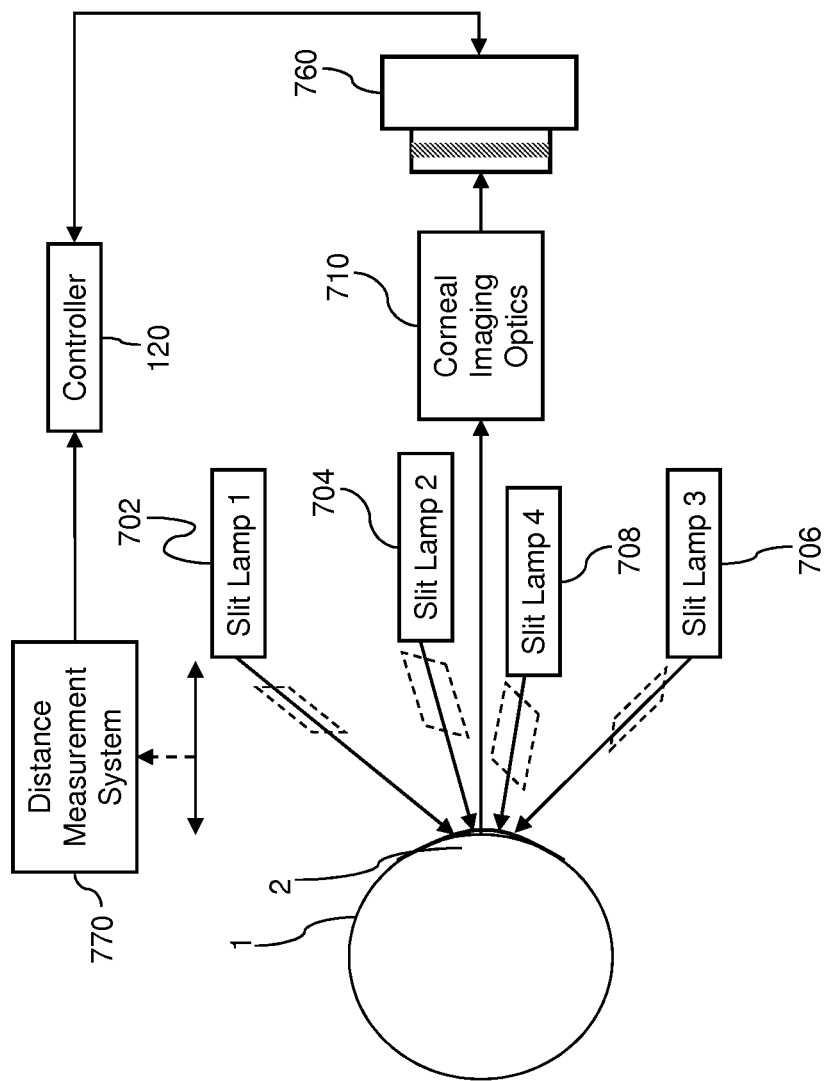
FIG. 7A illustrates a configuration utilizing multiple slit lamps to perform corneal topography and pachymetry.
FIG. 7B schematically illustrates an image of the cornea detected by the camera in a configuration utilizing four slit lamps.

FIG. 7A illustrates a configuration utilizing multiple slit lamps to perform corneal topography and pachymetry. The multiple slit lamp configuration may also provide targeting information to implementations of the feedback system 400. The multiple slit lamp configuration shown in FIG. 7A includes four slit lamps 702, 704, 706, 708. Each of the slit lamps 702, 704, 706, 708 may be similar to a conventional slit lamp employed in the field of optometry and ophthalmology to examine a patient's eye and to diagnose conditions existing in the layers of the eye. Each of the slit lamps may be adapted to illuminate a portion of the cornea 2 with light emerging from a slit. The slit may be an aperture having a narrow dimension and an elongated dimension. While the narrow dimension is finite, the light emerging from the slit lamp may be approximately considered as a sheet ("plane") of light, which illuminates a plane of the cornea 2. The four slit lamps 702, 704, 706, 708 may be oriented off-center from the optical axis of the cornea 2. For example, each may be oriented at 45° with respect to the corneal optical axis. Furthermore, the four slit lamps may be positioned such that they are equally spaced around the eye 1. As used herein, the corneal optical axis can be an axis extending outward from the center of the cornea 2 and passing through the center-point of the eye 1. In a substantially symmetrical cornea 2, the corneal optical axis can be defined by a ray extending outward from the center-point of the cornea 2 such that the corneal optics are substantially rotationally symmetric about the ray.

From the viewpoint of an observer facing the eye 1, from the behind the slit lamps 702, 704, 706, 708: the first slit lamp 702 may be positioned above the eye 1 and may direct a sheet of light downward at 45° with respect to the eye 1; the second slit lamp 704 may be positioned to the left of the eye 1 and may direct a sheet of light rightward at 45° with respect to the eye 1; the third slit lamp 706 may be positioned below the eye 1 and may direct a sheet of light upward at 45° with respect to the eye 1; the fourth slit lamp 708 may be positioned to the right of the eye 1 and may direct a sheet of light leftward at 45° with respect to the eye 1. Thus, in the schematic illustration provided in FIG. 7A, the second slit lamp 704 is positioned further into the page than the first slit lamp 702 and the third slit lamp 706. Similarly, the fourth slit lamp 708 is positioned further out of the page than the first slit lamp 702 and the third slit lamp 706.

The intensity pattern created by the multiple slit lamps illuminating the cornea 2 is directed to the camera 760 by the corneal imaging optics 710. The intensity pattern(s) detected by the camera 760 are then analyzed by the controller 120 to extract corneal topography and pachymetry information.

An illustrative schematic of an example intensity pattern created by the four slit lamp configuration is provided in FIG. 7B. The four slit lamps illuminate four curved lines on the cornea 2. The shape and thickness of the pattern observed on the cornea 2 provides information indicative of the shape of the corneal surface (i.e., corneal topography) and the thickness of the cornea 2 (i.e., corneal pachymetry). For example, the thickness of the bands of light observed with the camera 760 provides an indication of the corneal thickness, because the light observed at the camera 760 is reflected at both the posterior and anterior surfaces of the cornea 2. Thus, a thicker ("broader") line corresponds to a thicker corneal layer. When the precise parameters of the slit lamp orientation and position are known, including the thickness of the aperture of the slit lamps 702, 704, 706, 708, the observed corneal thickness can be approximated from the resulting intensity pattern. As the cornea 2 moves in and out relative to the position of the multiple slit lamps, the illumination pattern observed in the camera 760 changes as the sheets of light emitted from the slit lamps scan over the surface of the cornea 2. As the eye 1 moves relative to the slit lamps, the four curved lines sweep out a grid on the cornea 2. The curvature of the lines provide information indicative of the three dimensional profile of the eye surface. As the eye moves in and out with respect to the slit lamps 702, 704, 706, 708, a complete three dimensional profile of the corneal surface may be extracted. In some examples, look up tables can be empirically established to map observed characteristics to physical parameters (e.g., line thickness to corneal thickness, line curvature to corneal curvature, etc.).

FIG. 7B schematically illustrates an image of the cornea 2 detected by the camera 760 in a configuration utilizing four slit lamps. The light reflected from the cornea 2 toward the corneal imaging optics 710 can include light reflected from the outer corneal surface (i.e., the anterior surface) and from the posterior surface of the cornea 2. With reference to FIG. 7B, in an implementation where the slit lamp 702 is oriented above the eye 1 and is directing a sheet of light downward toward the eye 1, the cornea 2 is illuminated with a line 730 having a top edge 731 and a bottom edge 732. The top edge 731 is indicative of the anterior surface of the cornea 2, and the bottom edge 732 is indicative of the posterior surface of the cornea 2. Thus, the top edge 731 is nearest ("proximate") the slit lamp, while the bottom edge 732 is furthest ("distal") the slit lamp. Similarly, other lines on the cornea 2 have an edge closer to the direction of the associated slit lamp (a proximate edge), and an edge further from the direction of the associated slit lamp (a distal edge). Generally, the proximate edge(s) describe the anterior surface of the cornea 2 while the distal edge(s) describe the posterior surface of the cornea 2. By extracting the shape and/or position of the posterior (internal) surface of the cornea 2, and comparing with the shape and/or position of the anterior (outer) surface, the three-dimensional thickness of the cornea can be determined. Thus, the light emerging from the cornea 2 and directed toward the camera 760 includes information on the position of the posterior surface and therefore the thickness of the cornea 2.

The emerging light may also undergo spreading due to the diffusive optical characteristics of the corneal tissue, which influences the width(s) of the observed line(s). For example, observing relatively thicker line(s) can indicate a greater degree of optical diffusion, and thus greater corneal thickness. Ray tracing may also be employed to trace lines from slit lamps (e.g., the slit lamp 702) to the camera 760 to provide an estimate of anterior and posterior surfaces of cornea 2, and thus the shape and thickness of the cornea 2 at multiple locations (e.g., the locations illuminated by the slit lamps) may be extracted. By defining the shape and thickness of the cornea 2 at multiple locations, a three-dimensional profile of the cornea 2 can be determined. Using the camera 760, the surface estimates from the multiple slit lamp configuration may be matched to corneal surface estimates from an interferometry system to provide an even more accurate estimate of the full corneal topography and/or thickness.

By providing a three dimensional profile of the cornea 2, the controller 120 can determine the center position of the cornea 2 and/or the location and/or orientation of the corneal optical axis. The controller 120 can determine the center position by, for example, determining the apex of the three dimensional profile of the corneal surface. The determined center position may then be used in conjunction with adjustable optical and mechanical components to align any of the implementations of the feedback system 400 previously discussed.

The multiple slit lamp configuration illustrated in FIG. 7A also includes a distance measurement system 770 for determining the distance between the multiple slit lamps 702, 704, 706, 708 and the eye 1. In a configuration, the distance (or information indicative of the distance) is passed to the controller 120. The controller 120 uses the distance provided by the distance measurements system 770 in combination with the images from the camera 760 to get the radius of curvature of the cornea 2, and thus the optical power of the eye 1. The distance measurement can also allow for scaling the images observed on the camera 760 (e.g., mapping pixels to distances). The distance measurement system 770 may be implemented by two cameras focusing on the surface of the cornea 2, but oriented at an angle relative to one another, and separated by a known distance, such that the angle between the orientations of the two cameras when both are focused on the eye 1 provides an estimation of the distance according to standard trigonometric analysis. The distance measurement system 770 may be implemented as a high resolution camera capturing images from a known position. The high resolution camera may be oriented at approximately 90° to the optical axis of the eye 1, such that the edge of the eye 1 can be mapped to a pixel location of the high resolution camera, which corresponds to a distance from the slit lamps 702, 704, 706, 708. In addition, the distance measurement system 770 may be adapted according to an active ranging technique which uses reflected signals correlated with reference signals to measure time delays, such as a doppler, ultrasound, or optical ranging system.

Additionally, in a configuration where the positions of the slit lamps 702, 704, 706, 708 are well known, the distance may be estimated directly from the slit lamps, camera, and optical elements illustrated in FIG. 7A. Such a distance measurement may be performed by finely adjusting the position of the eye 1 (e.g., via a positioning system mounted to a bite plate or head restraint similar to the three dimensional positioner 672 shown in FIG. 7A) until the intensity pattern observed by the camera 760 is a characteristic pattern that is indicative of a known distance. For example, the characteristics pattern can be a cross centered on the apex of the cornea 2 formed by an overlap between the light of the upper and lower slit lamps 702, 706, and an overlap from the light of the side slit lamps 704, 708). In other examples, the position of the slit lamps and associated optics can be adjusted by translating the slit lamps toward and away from the eye 1, in a direction generally parallel to the corneal optical axis, until the characteristic pattern is detected. The position of the eye 1—or the position of the slit lamps and associated optics—may then be adjusted by known steps relative to the known distance as desired.

In addition to utilizing the four slit lamp apparatus described in connection with FIGS. 7A and 7B for targeting, the configuration can be utilized to illuminate cross-section portions of the eye 1 with excitation light (e.g., the excitation light 642 in FIG. 6). Similar to the description of the single thin slit excitation source 640 in FIG. 6, the four slit lamps 702, 704, 706, 708 can be flashed to periodically illuminate the eye 1 with light sufficient to excite a photo-active marker applied to the eye 1. The four slit lamp configuration can advantageously simultaneously or serially excite distinct cross-sectional portions of the eye 1 to allow the controller 120 to estimate the distribution of the photo-active marker 530 throughout the tissue of the eye 1. For example, the controller 120 can estimate the full distribution of the photo-active marker from the observed intensity from four illuminated regions (e.g., the illuminated lines shown in FIG. 7B) by interpolating between measurement points. The multiple slit lamp configuration also allows for the controller 120 to analyze the captured images to determine the distribution of the photo-active marker 530 as a function of depth within the tissue of the eye 1. An example of extracting distribution information by combining cross-sectional intensity profiles with solutions to the diffusion equation is provided in connection with equation 1 and 2 below.

Figure 8A:
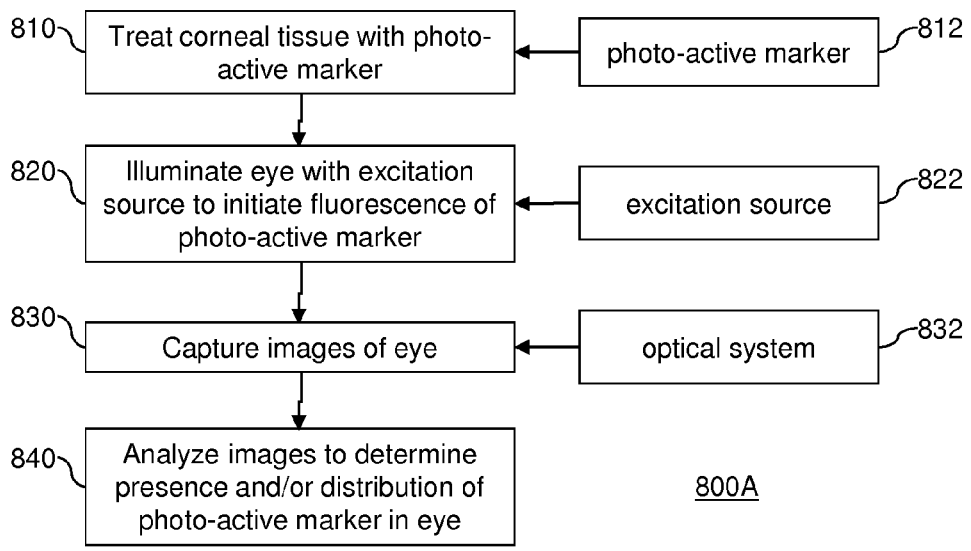
FIG. 8A provides an exemplary embodiment according to the present disclosure.

FIG. 8A provides an exemplary embodiment 800A according to the present disclosure. With reference to the systems 500 and 600 in FIGS. 5 and 6, respectively, a photo-active marker 812 is applied to corneal tissue of an eye 1 (810). The eye 1 is illuminated with an excitation source 822 to initiate fluorescence of photo-active marker (820). Images of the eye 1 are captured with an optical system 832 (830). The optical system 832 generally includes an image capture device having a photo sensitive detector, such as a CCD detector. The images are analyzed to determine the presence and/or distribution of the photo-active marker 812 in the eye 1 (840).

Figure 8B:
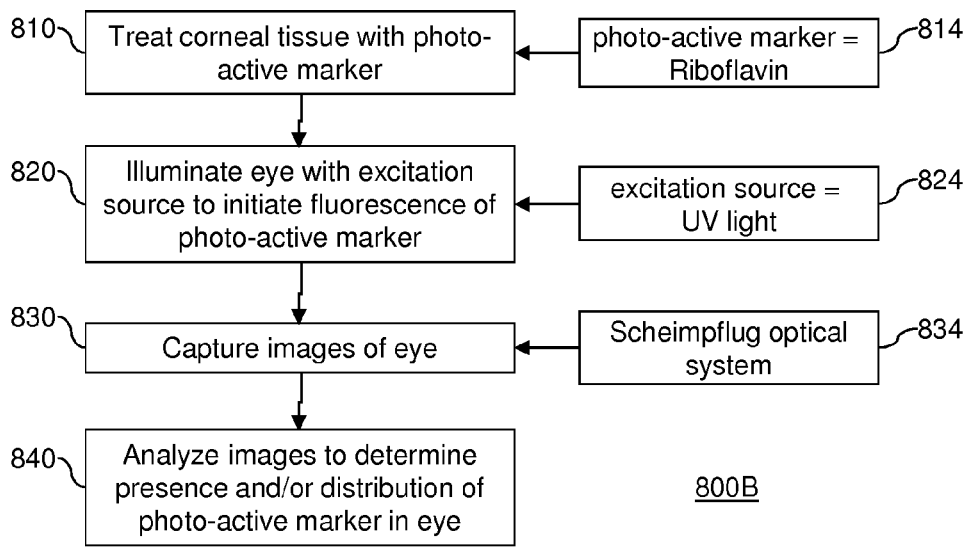
FIG. 8B provides another exemplary embodiment with reference to aspects of the present disclosure.

In FIG. 8B, another exemplary embodiment 800B is illustrated with reference to aspects of the present disclosure. In the embodiment 800B, the photo-active marker can be Riboflavin 814, the excitation source can be UV light 824, and the optical system can be a Scheimpflug system 834. However, it is understood that aspects of the present disclosure are not so limited and can include implementations where the photo-active marker 812 is Rose Bengal or another substance suitable for application to the eye 1 that is capable of exhibiting fluorescence upon excitation with wavelengths suitable for being applied to an eye 1. In addition, the excitation source 822 can be appropriately chosen to correspond to the photo-active marker 812 such that the photo-active marker 812 is excited and caused to fluoresce by the excitation source 822. Furthermore, the optical system 834 can include one or more slit lamps, a Scheimpflug system, or combinations thereof to provide images that characterize the intensity of the photo-active marker 812. The optical system 832 desirably allows for imaging the intensity of the photo-active marker 812 along cross-sectional portions of the eye 1 in order to extract information indicative of the distribution of the photo-active marker 812 at depths of the eye 1.

Aspects of the present disclosure further provide for repeatedly implementing the embodiment 800A to study the distribution of the photo-active marker 812 in the eye 1 over time, and to extract information indicative of the rate of uptake of the photo-active marker 812. In some implementations, the presence, distribution, and/or uptake rate of the photo-active marker 812 can be indicative of a disease pathology of the eye 1.

Figure 9:
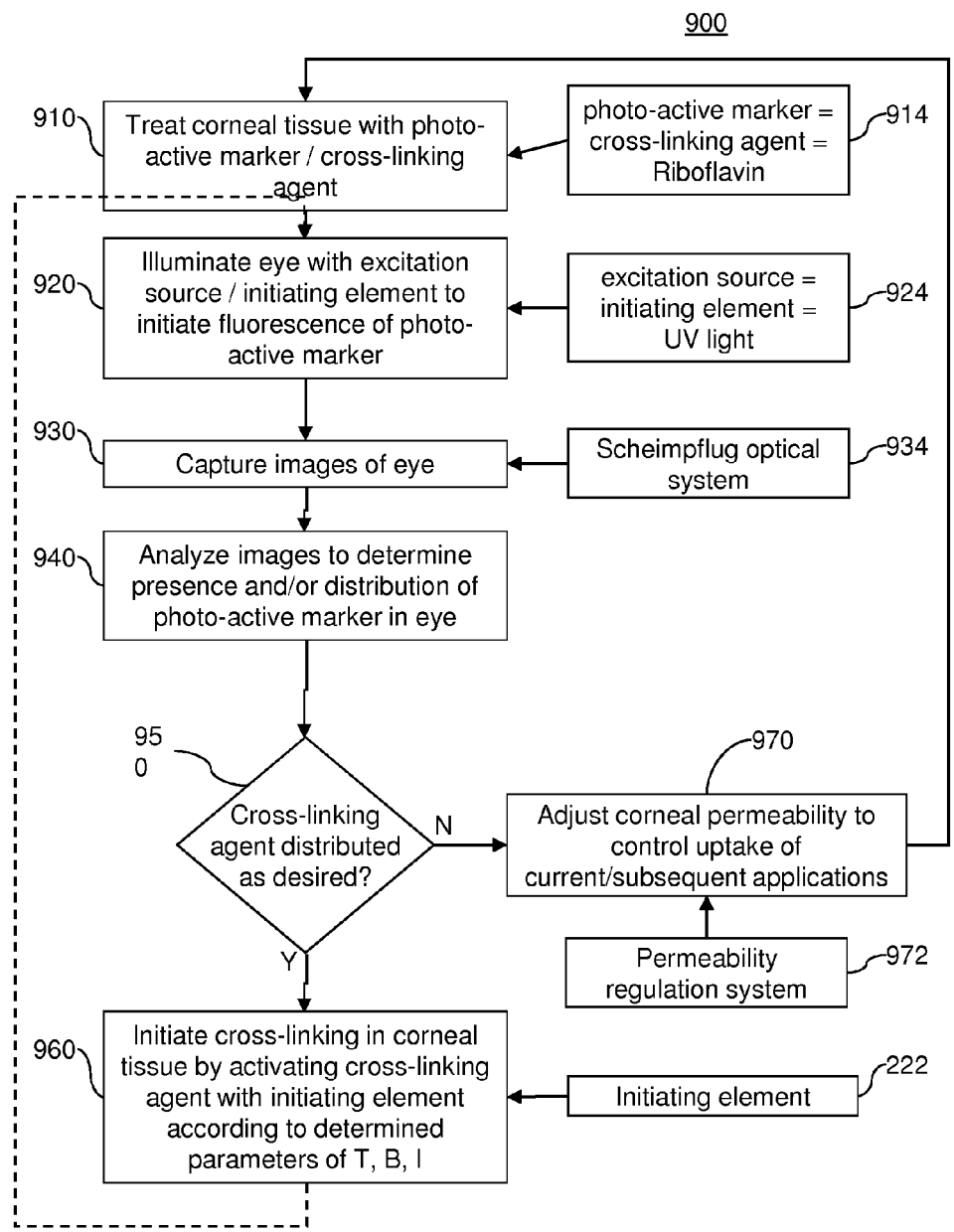
FIG. 9 illustrates an implementation of the present disclosure that provides for monitoring the distribution of a cross-linking agent which is also a photo-active marker in order to provide feedback information while initiating cross-linking within an eye.

FIG. 9 illustrates an implementation 900 of the present disclosure that provides for monitoring the distribution of a cross-linking agent 914 which is also a photo-active marker in order to provide feedback information while initiating cross-linking within an eye 1. In block 910, the corneal tissue is treated with the photo-active marker/cross-linking agent 914. For example purposes, the marker/agent 914 can be Riboflavin, but it is understood that other suitable treatment options can be implemented. In block 920, the eye 1 is illuminated with excitation source/initiating element 924 to initiate fluorescence of photo-active marker. For example purposes the excitation source/initiating element 924 can be UV light, such as 365 nm to 370 nm UVA light, but it understood that other suitable treatment options can be implemented. In block 930 images of the eye 1 are captured using a Scheimpflug optical system 934 and an associated camera to capture a series of cross-sectional images of the eye 1. In block 940, the captured images are analyzed to determine the presence and/or distribution of photo-active marker 914 in the eye 1.

In the decision block 950, the determined distribution of the marker/agent 914 is compared with a desired distribution of the cross-linking agent. If the distribution is as desired, cross-linking is initiated in block 960. If the distribution is not as desired, the distribution can be adjusted prior to initiating cross-linking. The distribution of the marker/agent 914 can be adjusted by modifying the permeability (i.e., the susceptibility to uptake) of the cornea 2 in block 970 and returning to block 910 to apply additional marker/agent 914. The adjustment to the corneal permeability (970) can be carried out via a permeability regulation system 972, such as, for example, an infrared, microwave, or laser system that applies a pattern of radiation to the cornea to heat the corneal tissue according to the applied pattern. Because the permeability of the corneal tissue is enhanced at increased temperatures, the permeability of the corneal tissue is modified according to the applied pattern of heat energy. The permeability regulation system 972 can additionally or alternatively include, for example, an ultrasound system to apply ultrasound energy to increase the permeability of the corneal tissue, and which can optionally include microspheres to direct and/or focus the ultrasound energy. For example, the permeability regulation system 972 can be a thermokeratoplasty applicator for conveying microwave heat energy to the cornea 2. Exemplary permeability regulation systems and schemes for operating the same are described in U.S. patent application Ser. No. 13/475,175, filed May 18, 2012, the contents of which is hereby incorporated herein by reference in its entirety. In some examples, the permeability regulation system includes an infrared ("IR") radiation source that is directed to a digital micro-mirror device ("DMD") to selectively reflect the infrared radiation and provide a time-averaged beam profile according to a desired pixelated pattern. For example, the DMD for patterning the IR to adjust the permeability of the corneal tissue can also be employed to pattern UVA on the corneal tissue to activate cross-linking (e.g., the DMD 344 of FIG. 3 and/or the patterning light delivery optical system 610 of FIG. 6). Thus, in some embodiments, a UVA source and an IR source can be arranged to be convey radiation incident on a common digital micro-mirror device, such as via one or more adjustable mirror(s) and/or other optical elements to selectively block radiation from the UVA and/or IR sources from reaching the DMD, for example. Alternatively, patterns of radiation, e.g., from UVA and/or IR sources, may be applied with a scanning mirror system.

Furthermore, while not separately illustrated in the embodiment 900 of FIG. 9, the permeability of the corneal tissue can be adjusted via the permeability regulation system 972 prior to the initial instillation of the marker/agent 914 in block 910. For example, an initial patterned application of heat energy (e.g., a pixelated pattern of IR radiation reflected from a DMD) can be applied to provide preferential uptake of the applied marker/agent 914 in desired regions. For example, region(s) of the corneal tissue with relatively greater corneal thickness, epithelial thickness, etc., and/or region(s) where relatively greater cross-linking is desired to occur according to a determined treatment plan, can be modified so as to increase the uptake rate and/or capacity of the corneal tissue to the marker/agent 914.

Additionally or alternatively, the distribution of the marker/agent 914 can be adjusted by applying a reverse osmotic fluid to the surface 2A of the cornea 2 to draw the marker/agent 914 away from the surface 2A or by applying quenching agent to inhibit, deactivate, or degrade the marker/agent 914. Example quenching agents and methods of utilizing them are described in U.S. patent application Ser. No. 13/475,175, filed May 18, 2012. Generally, applying either quenching agents, reverse osmotic fluids, or other chemical agents to the eye 1 can modify the distribution of the marker/agent 914 within the eye 1. Applying the various agents can be utilized to modify the distribution prior to activation of cross-linking, or can be utilized to modify the rate of cross-linking reactions as a function of depth within the eye 1. For example, applying a reverse-osmotic fluid may decrease cross-linking near the surface 2A. Additionally or alternatively, applying a quenching agent may inhibit the marker/agent 914 from being sensitized to react and thereby generate cross-linking. To create desired reaction rates and/or distributions, the concentrations of the applied substances and the duration of their application can also be adjusted. Generally, the distribution of the marker/agent 914 and/or the efficacy of the marker/agent 914 to act as a sensitizer to generate cross-linking reactions can be adjusted as a function of depth within the eye 1 through the use of quenching agents, reverse-osmotic fluids, other ophthalmological fluids, and the like alone or in combination with the permeability regulation system 972 of FIG. 9.

Once the distribution is determined to be as desired in block 950, block 960 can be carried out. The cross-linking block 960 can be carried out to apply the initiating element 222 according to a predetermined set of parameters including duration ("T"), spectral bandwidth ("B"), quencher ("Q"), and intensity pattern ("I"). The cross-linking block 960 can also be carried out in an iterative fashion to repeatedly apply the initiating element 222 to the eye 1 a set number of times ("N") with B, T, I all fixed. Additionally or alternatively, the cross-linking block 960 can call for repeated application of the initiating element 222 according to distinct parameters during duration(s) ("T[k]"), spectral bandwidth(s) ("B[k]"), quencher(s) ("Q[k]"), and intensity pattern(s) ("I[k]"), with k defined from 1 to N and each of the respective T[k], B[k], Q[k], and I[k] being optionally dis-similar from one another. Furthermore, in implementations where the cross-linking block 960 is itself iterative, the cross-linking block 960 can itself be interrupted to provide a fluorescence dosimetry reading (e.g., return to block 920) to monitor the distribution of the marker/agent before completing the cross-linking block 960.

Furthermore, some embodiments of the present disclosure provide for capturing cross-sectional views of the corneal tissue via an optical coherence tomography ("OCT") system. By photo-activating cross-linking agent and providing suitable filters over the light detecting portions of the OCT system, the cross-sectional views captured by the OCT system can be indicative of the distribution of photo-activated cross-linking agent (or another photo-activated marker) within the corneal tissue. Exemplary OCT systems are described, for example, in U.S. Provisional Patent Application Ser. No. 61/542,269, filed Oct. 2, 2011; U.S. Provisional Patent Application Ser. No. 61/550,576, filed Oct. 24, 2011; and U.S. Provisional Patent Application Ser. No. 61/597,137, filed Feb. 9, 2012, the contents of each of these applications being incorporated herein by reference in its entirety. Thus, aspects of the present disclosure generally provide for determining a distribution of photo-active cross-linking agent according to cross-sectional images of the cornea while the cross-linking agent undergoes fluorescence. The distribution of cross-linking agent within the tissue can be determined based on the cross-sectional intensity profiles such as described in connection with equations 1 and 2, for example.

While it is appreciated that aspects of the present disclosure for measuring a distribution of a photo-active marker through fluorescence dosimetry are not limited to particular photo-active markers, excitation sources, or optical systems for capturing images, an experimental apparatus is described next to illustrate an exemplary measurement scheme and system therefore in connection with FIGS. 10A and 10B.

Figure 10A:
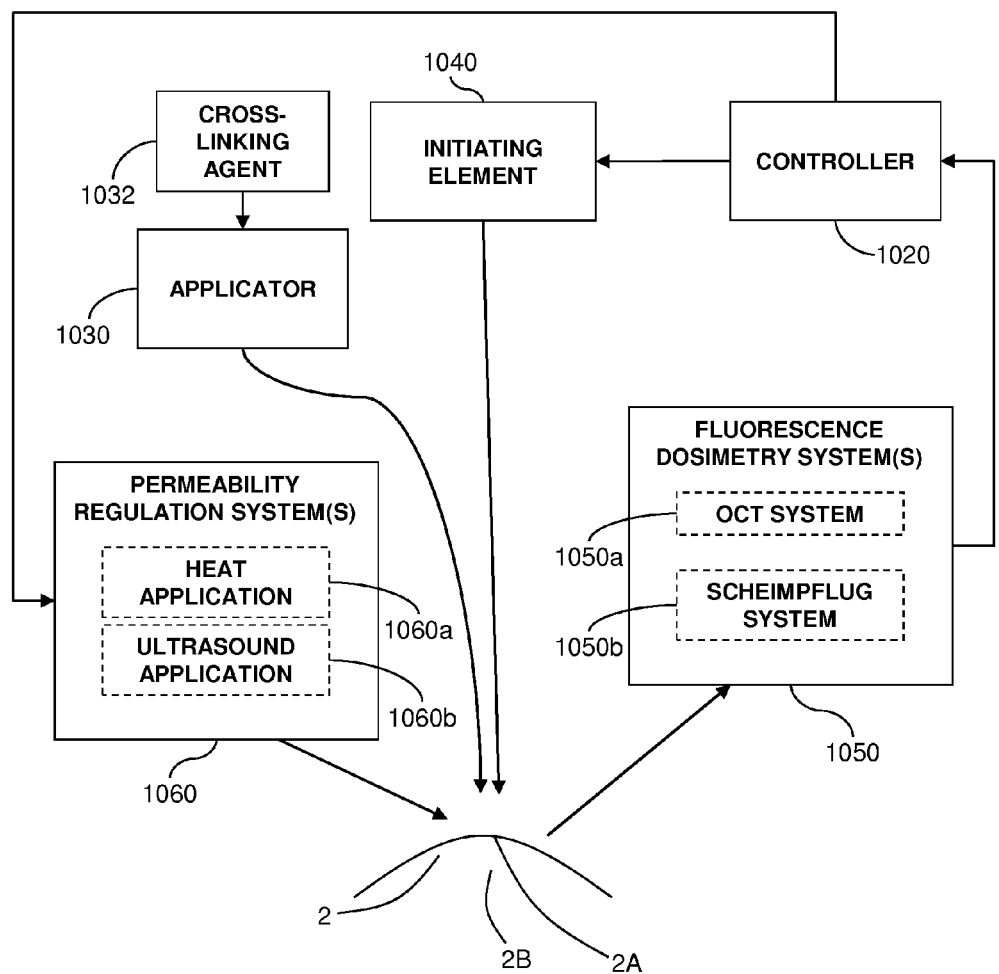
FIG. 10A is a block diagram of an exemplary system for controlling the distribution of the cross-linking agent within the eye through permeability regulation system(s) according to feedback information from fluorescence dosimetry feedback system(s).

FIG. 10A is a block diagram of an exemplary system 1000a for controlling the distribution of the cross-linking agent 1032 within the eye 1 through permeability regulation system(s) 1060 according to feedback information from fluorescence dosimetry feedback system(s) 1050. The system 1000a includes a controller 1020, a drug application device 1030, and an initiating element 1040 (and any associated optical elements for conveying the initiating element 1040 to the eye 1). Similar to the system 100 described in connection with FIG. 1, the controller 1020 operates the initiating element 1040 and/or associated optical elements to apply the initiating element 1040 to the eye 1 according to specified intensity patterns, energy doses, and/or timing intervals. In the system 1000a, the controller 1020 is configured to control the permeability regulation system(s) 1060 to provide a desired three dimensional distribution of the cross-linking agent 1032 within the corneal tissue 2. For example, the controller 1020 can operate the system 1000a according to any of the methods provided by the embodiments described above in connection with FIGS. 8-9, for example.

In an exemplary operation of the system 1000a, the permeability regulation system(s) 1060 apply energy to the corneal tissue 2 to increase the permeability of the corneal tissue 2 to the cross-linking agent 1032. The permeability regulation system(s) 1060 can adjust the permeability of the corneal tissue 2 via heat application 1060a and/or ultrasound energy application 1060b. In some examples, the heat application 1060a can be achieved via a laser radiation system, a near infrared radiation system, a microwave thermokeratoplasty system, etc. Exemplary permeability regulation systems, and operation schemes therefore are described, by way of example, in U.S. patent application Ser. No. 13/475,175, filed May 18, 2012. Thus, the controller 1020 operates the permeability regulation system(s) 1060 to control the permeability (e.g., uptake rate and/or amount) of the corneal tissue 2 to the cross-linking agent 1032. By applying energy from the permeability regulation system(s) 1060 according to a non-uniform pattern, the permeability of the corneal tissue 2 can be adjusted with some regions becoming relatively more permeable to the cross-linking agent than other regions, which regions are based on the applied non-uniform pattern. Modifying the corneal permeability according to a non-uniform pattern allows the cross-linking agent 1032 that diffuses into the corneal tissue 2 to penetrate ("absorb") according to a non-uniform pattern corresponding to the non-uniform pattern of the permeability regulation system(s) 1060.

The system 1000a further includes the fluorescence dosimetry system(s) 1050. The dosimetry system(s) 1050 are configured to dynamically monitor the distribution of cross-linking agent in the corneal tissue 2. Generally, the dosimetry system(s) 1060 include sensors (e.g., cameras) to measure characteristics of the corneal tissue 2 (e.g., images indicating fluorescence activity), and outputs to convey signals indicative of the measured characteristics to the controller 1020 such that the distribution of the cross-linking agent can be determined by analyzing the measured characteristics. The dosimetry system(s) 1060 can capture cross-sectional images of fluorescence activity (which indicates the distribution of the cross-linking agent along the cross-sectional region) via an Optical Coherence Tomography ("OCT") system 1050a and/or a Scheimpflug system 1050b.

Additionally, the system 1000a can optionally include an additional feedback system (not shown) for monitoring biomechanical properties of the corneal tissue 2. For example, the feedback system(s) can monitor observable factors influencing (or indicative of) the distribution of cross-linking agent or the progress of cross-linking activity within the corneal tissue 2. Generally, the feedback system(s) include sensors to measure characteristics of the corneal tissue 2, and outputs to convey signals indicative of the measured characteristics to the controller 1020. In some examples, feedback system(s) include an interferometry system, a multi-camera Scheimpflug system, an Ocular Coherence Tomography (OCT) system, a Supersonic Shear Imaging (SSI) system, or another monitoring system for characterizing biomechanical properties of the eye 1. For example, an interferometry system can characterize the corneal topography by comparing interference patterns of light reflected from the corneal surface with light reflected from a reference surface. Observing the corneal topography over time allows for characterization of the dynamic deformation of the corneal tissue 2 in response to subtle perturbations, such as changes in intraocular pressure, external stimuli, etc. The rate and/or amount of deformation provide an indication of biomechanical strength or stiffness (e.g., a measure of the resistance to deformation) of the corneal tissue. Thus, feedback systems operative to provide indications of the biomechanical strength of the corneal tissue 2 can indicate the progress of cross-linking activity in the eye, and thus indicate the need for additional cross-linking activity. The feedback system can optionally include systems for detecting additional biomechanical properties of the eye 1, such as corneal thickness. Further the feedback system may include a video system for monitoring the position of the cornea 2 and aligning optical elements conveying the initiating element 1040 according to the position information.

The feedback system can alternatively or additionally include an OCT system or Scheimpflug system configured to dynamically characterize the deformation response of corneal tissue 2 to subtle perturbations and thereby determine the biomechanical strength of the corneal tissue. Systems and methods relating to monitoring the distribution of cross-linking agent and aspects of cross-linking activity are described, for example, in U.S. patent application Ser. No.

13/051,699, filed Mar. 18, 2011; U.S. Provisional Patent Application No. 61/492,553, filed Jun. 2, 2011; U.S. Provisional Patent Application No. 61/542,269, filed Oct. 2, 2011; U.S. Provisional Patent Application No. 61/550,576, filed Oct. 24, 2011; and U.S. Provisional Patent Application No. 61/597,137, filed Feb. 9, 2012; the contents of these applications being incorporated entirely herein by reference.

Furthermore, the distribution of cross-linking agent and aspects of cross-linking activity may be dynamically monitored via the dosimetry system(s) 1060. For example, indications of the presence and/or distribution of the cross-linking agent 1032 within the cornea 2 may be detected via fluorescence of the cross-linking agent 1032. In some examples, the distribution of the cross-linking agent 1032 can be characterized in three dimensions by observing fluorescence at multiple distinct focal depths within the corneal tissue 2. As such, the application and distribution of the cross-linking agent 1032 may be controlled in response to the dynamic monitoring by, for example, adjusting the permeability of the corneal tissue 2 via the permeability regulation system(s) 1060.

Additionally or alternatively, diffusion influencing compounds can be applied to the cornea 2 via the applicator 1030 to urge the cross-linking agent 1032 to further depths within the cornea 2 (e.g., a neutral compound) or to draw the cross-linking agent 1032 from the cornea 2 (e.g., a reverse osmotic fluid). Furthermore, cross-linking agent 1032 within the corneal tissue 2 can be quenched following a cross-linking treatment by a quenching agent applied via the drug application device 132, as described in connection with FIG. 14.

In some embodiments, feedback information from the feedback system(s) and/or fluorescence dosimetry system(s) 1050 can then be used to develop a treatment plan or dynamically adjust a treatment plan that is suited to the monitored characteristics of the corneal tissue 2. The treatment plan can be characterized by one or more applications of the cross-linking agent 1032 to achieve desired distributions within the cornea 2 and one or more energy doses of the initiating element 1040 delivered via optical elements according to desired patterns (e.g., via a DMD device or a scanning mirror system) to controllably activate cross-linking in the corneal tissue 2. Exemplary systems and methods for controlling the activation of the cross-linking agent 1032 by precisely delivering the initiating element both spatially and temporally, and optionally according to information received from a feedback system are provided in U.S. patent Ser. No. 13/051,699, filed Mar. 18, 2011, and which claims priority to U.S. Provisional Application No. 61/315,840, filed Mar. 19, 2010; U.S. Provisional Application No. 61/319,111, filed Mar. 30, 2010; U.S. Provisional Application No. 61/326,527, filed Apr. 21, 2010; U.S. Provisional Application No. 61/328,138, filed Apr. 26, 2010; U.S. Provisional Application No. 61/377,024, filed Aug. 25, 2010; U.S. Provisional Application No. 61/388,963, filed Oct. 1, 2010; U.S. Provisional Application No. 61/409,103, filed Nov. 1, 2010; and U.S. Provisional Application No. 61/423,375, filed Dec. 15, 2010, the contents of these applications being incorporated entirely herein by reference. These and other techniques may be combined with the permeability regulation system(s) 1520 and/or fluorescence dosimetry system(s) 1050 to control the diffusion of the cross-linking agent 1032 into selected corneal regions according to a desired distribution and thereby generate cross-linking activity at selected regions of the corneal tissue 2.

Figure 10B:
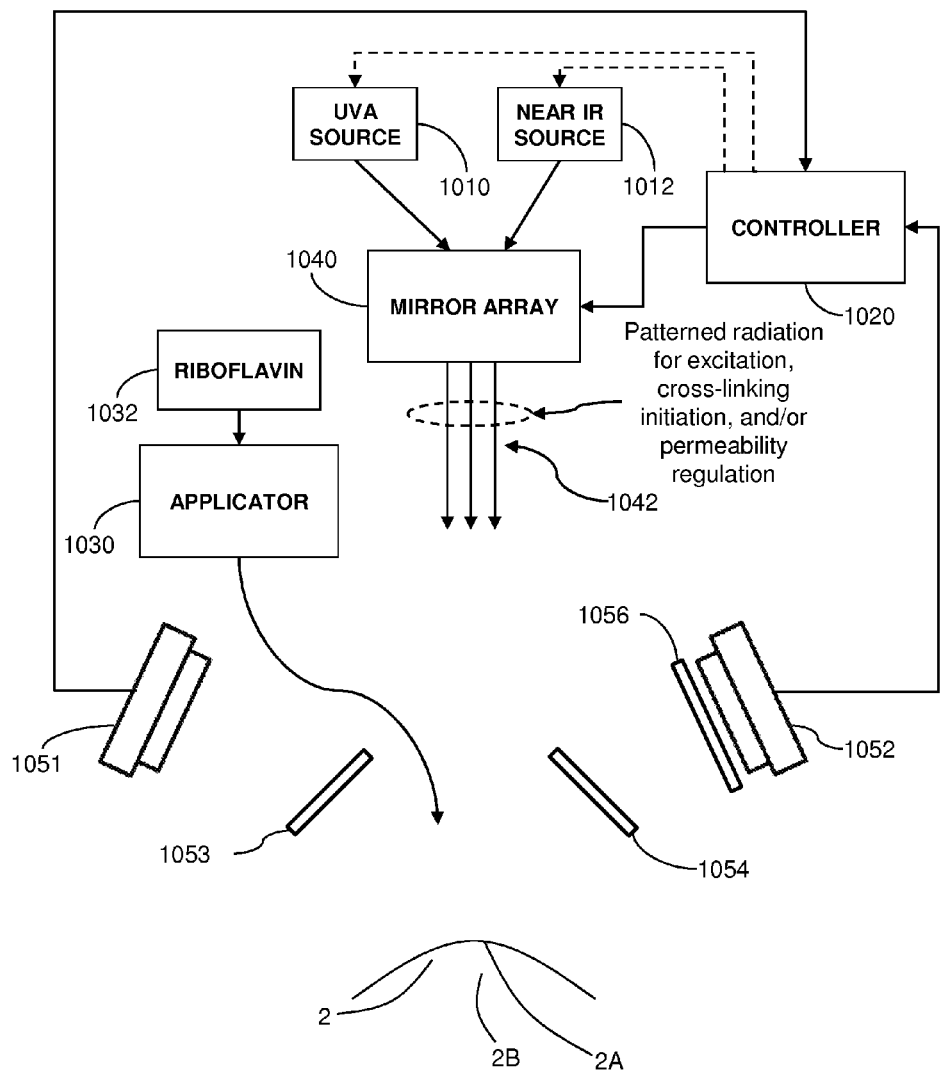
FIG. 10B is a cross-linking agent distribution regulation system that includes a dual off-axis Scheimpflug fluorescence dosimetry system.

FIG. 10B is a cross-linking agent distribution regulation system 1000b that includes a dual off-axis Scheimpflug fluorescence dosimetry system. The system 1000b includes a first and second camera 1051, 1052 and a first and second lens 1053, 1054 for focusing the image plane of the cameras 1051, 1052 on the eye 1 with a depth of focus sufficient to detect fluorescent energy from both the posterior and anterior surfaces of the cornea 2. In some examples, the cameras 1051, 1052 are situated on opposing sides of the eye 1 symmetrically about the corneal optical axis and each oriented with their respective imaging planes at an acute angle with the corneal optical axis. The two cameras 1051, 1052 can optionally rotate about an axis aligned (at least approximately) with the corneal optical axis to thereby capture images at multiple cross-sectional perspectives of the cornea 2. Furthermore, a filter 1056 is situated to selectively block light observed at the second camera 1052 such that the second camera 1052 receives the fluorescent light while the exciting light is substantially blocked. Filtering one camera (e.g., the second camera 1052) while leaving the other camera unfiltered (e.g., the first camera 1051) allows for comparison between the filtered and unfiltered images. In some examples another filter can be provided to allow both cameras 1051, 1052 to receive the fluorescent light while blocking the exciting light. The images from the two cameras 1051, 1052 are directed to the controller 120 where the images are analyzed and the distribution of the cross-linking agent is determined based on the captured images.

Once the distribution of cross-linking agent (e.g., Riboflavin 1032) is determined, distribution can be adjusted by applying additional cross-linking agent via the applicator 1030 and/or by adjusting the permeability of the corneal tissue 2 to the cross-linking agent. Systems and methods for adjusting the permeability of the corneal tissue 2 via permeability regulation systems are discussed further herein. In some examples, the permeability of the corneal tissue can be modified by applying heat energy to the corneal tissue, such as heat energy delivered via microwave radiation and/or near infrared radiation. As illustrated in the system 1000, a near infrared radiation source 1012 can be directed to the mirror array 1040 to provide a pixelated pattern of near IR radiation to the cornea 2 according to a desired modification in permeability prior to, during, and/or after instillation of the Riboflavin 1032 via the applicator 1030. For example, where the controller 1020 determines, based on the received cross-sectional images from the rotating Scheimpflug system (i.e., the cameras 1051, 1052; lenses 1053, 1054; etc.), that the concentration of cross-linking agent is too low in identified regions of the corneal tissue 2, the UVA source 1010 can be turned off (or directed away from the mirror array 1040) and the near IR light source 1012 can be directed to the mirror array 1042 so as to treat the identified low concentration regions with additional near IR, so as to increase the permeability of those regions. The distribution of the cross-linking agent can be continuously monitored via the system 1000b until a desired distribution is achieved and cross-linking can be initiated. In some examples, the mirror array 1040 can then provide a third purpose: to initiate the cross-linking by directing light from the UVA source 1010 to the cornea 2 according to a desired pattern of cross-linking initiation.

Figure 11A:
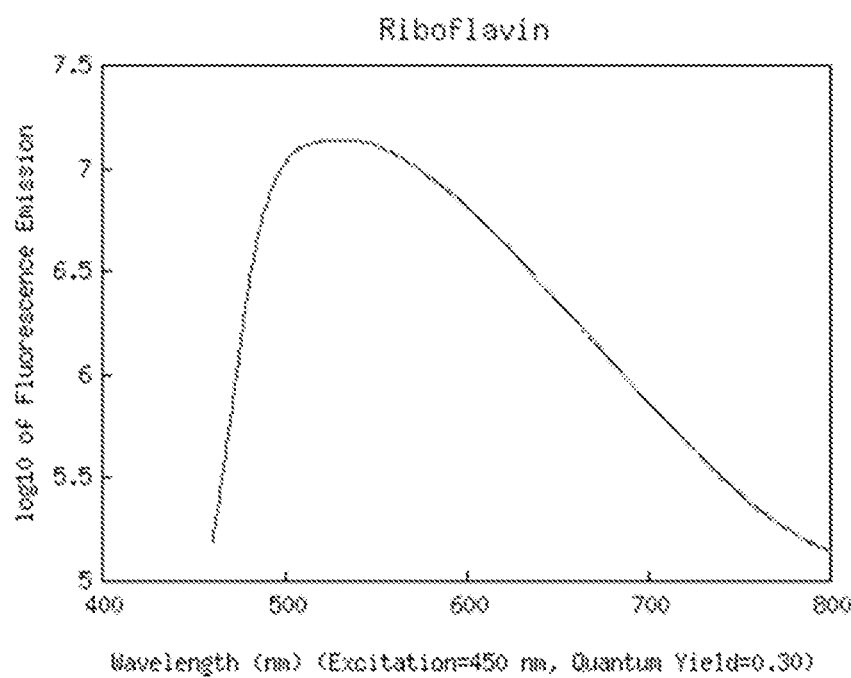
FIG. 11A illustrates an emission spectrum for Riboflavin when excited by a 450 nm excitation source.

In an experimental setup, the Galilei Dual Scheimpflug Analyzer from Ziemer was used to perform experiments to detect the presence of Riboflavin in porcine corneas through a filter in front of one of the detectors in the Scheimpflug analyzer. The Dual Scheimpflug Analyzer has two detectors that rotate 180° taking several spokes (ranging from 16 to 60 spokes) of the corneal tissue illuminated by 470 nm light through a slit lamp aperture. At that wavelength (470 nm), the Riboflavin present in the cornea is excited and fluoresces at a peak of approximately 525 nm as seen in the graph shown in FIG. 11A, which illustrates an emission spectrum for Riboflavin when excited by a 450 nm excitation source.

Figure 11B:
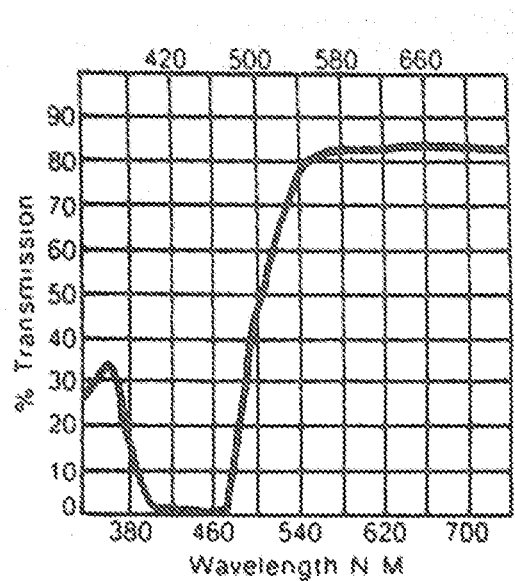
FIG. 11B illustrates the transmission spectrum for the Straw colored filter.

A Straw colored filter (Cinegel, Rosco) is used to filter the exciting light (i.e., the 470 nm light), while allowing the fluorescence (i.e., the 525 nm light) to reach the detector. This is illustrated by the graph shown in FIG. 11B, which illustrates the transmission spectrum for the Straw colored filter utilized.

The experimental procedure called for debriding the epithelium of a porcine eye (1 day post-mortem) and soaking the eye in saline to inflate the eye to about 15 mmHg. The effect of varying the soak time of the eye was studied as follows. A Scheimpflug image (or series of images) was taken with the Straw filter on one of the cameras, while the other camera was not filtered, to thereby obtain two images: one with the filter and one without. Obtaining two images, one filtered and one not, allows for comparing the full spectrum of excitation and emission (unfiltered) versus emission only (filtered). Drops of 0.1% Riboflavin-5-phosphate in 20% dextran solution were placed on the eye (providing a reservoir of riboflavin solution) and allowed to pre-soak for 9 minutes. After pre-soak, the eye was placed in front of the Scheimpflug analyzer and another image (or series of images) was captured. Riboflavin was then dropped on the eye once again for another 6 minutes and an image (or series of images) was captured. The instillation and Scheimpflug image capture procedure was repeated again for 15 and 21 minutes of pre-soak times. The results of this procedure to extract the concentration of Riboflavin as a function of distance within the eye are presented in FIG. 12. The analysis of the images to extract the Riboflavin distribution, such as the concentration of Riboflavin as a function of distance into the cornea is described below in connection with equations 1 and 2.

The effect of varying the concentration of Riboflavin in the treatment solution was also studied. A porcine eye (1 day post-mortem) was debrided of its epithelium and inflated to around 15 mmHg with saline. As before a Scheimpflug image (or series of images) is captured with the Straw filter on one of the cameras to obtain two images: one with the filter and one without. Drops of 0.1% Riboflavin-5-phosphate in 20% dextran solution were placed on the eye (providing a reservoir of riboflavin solution) and allowed to pre-soak for 15 minutes. After the pre-soak, the eye was placed in front of the Scheimpflug analyzer and another image (or series of images) was captured to determine the distribution of the Riboflavin within the cornea according to the observed pattern of fluorescence. This procedure was repeated with two more eyes for 15 minutes pre-soak times using 0.25% and 0.5% riboflavin-5-phosphate solutions respectively. The results of this procedure to extract the concentration of Riboflavin as a function of distance within the eye at the different Riboflavin concentrations are presented in FIG. 13. The analysis of the images to extract the distribution is described below in connection with equations 1 and 2.

The effect on the distribution of Riboflavin due to the application of a quenching agent to the eye following a Riboflavin pre-soak was also studied. Ascorbic acid can be considered a fluorescence quenching agent for Riboflavin due to its tendency to block the light reaction (e.g., photo-activation). However, as discussed above, several different substances can be utilized as quenching agents to inhibit the photo-activation of a cross-linking agent, or to degrade the cross-linking agent such that it is no longer photo-active. A porcine eye (1 day post-mortem) was debrided of its epithelium and inflated to around 15 mmHg with saline. A Scheimpflug image was taken with the filter on one of the cameras to obtain two images: one with the filter and one without. Drops of 0.1% Riboflavin-5-phosphate in saline solution were placed on the eye (providing a reservoir of riboflavin solution) and allowed to pre-soak for 30 minutes. After the pre-soak, the eye was placed in front of the Scheimpflug analyzer and another image (or series of images) was captured to determine the distribution of Riboflavin based on the detected pattern of fluorescence within the cornea. Drops of 1% ascorbic acid were then placed on the eye (providing a reservoir) for 5 minutes and another image (or series of images) was captured. This was repeated two more times to obtain images after 5, 10, and 15 minutes of ascorbic acid soak time. This same experiment was repeated on one more eye to investigate the repeatability of the observed results. Furthermore, the results were compared with a control eye where all the experimental procedures were similar except for using distilled water instead of ascorbic acid. The results of this procedure to extract the concentration of Riboflavin as a function of distance within the eye after applying a quenching agent for varying durations are presented in FIGS. 14, 15A and 15B. The analysis of the images to extract the distribution is described below in connection with equations 1 and 2.

The effect of applying UVA radiation (e.g., light with a wavelength of 365 nm to 370 nm) to an eye pre-soaked with Riboflavin was also studied. A porcine eye (1 day post-mortem) was debrided of its epithelium and inflated to around 15 mmHg with saline. A Scheimpflug image was taken with the Straw filter on one of the cameras to obtain two images: one with the filter and one without. Drops of 0.1% Riboflavin-5-phosphate in saline solution was placed on the eye (providing a reservoir of Riboflavin solution) and allowed to pre-soak for 30 minutes. After the pre-soak, the eye was placed in front of the Scheimpflug analyzer and another image (or series of images) was captured to determine the distribution of Riboflavin according to the observed fluorescence within the cornea. The eye was then placed under a UVA light source (365 nm) at 30 mW/cm$^2$ for one minute and another image was then taken. The UVA light source can be, for example, a light emitting diode (LED). This was repeated two more times to obtain images after one, two, and three minutes of UVA irradiation. This same experiment was repeated on two more eyes and results were averaged. In addition, three eyes were used as control where all the experimental procedures were similar except for keeping the UVA turned off. The results of this procedure to extract the concentration of Riboflavin as a function of distance within the eye after applying varying amounts of UVA light to the eye are presented in FIGS. 16A and 16B. The analysis of the images to extract the distribution is described below in connection with equations 1 and 2.

To analyze the effects described above, images from the Scheimpflug image capture system were exported and analyzed. Using ImageJ software (http://rsbweb.nih.gov/ij/), cross-sectional intensity profiles are plotted for each image for both before and after applying Riboflavin. Images of cornea with no Riboflavin provide the baseline intensities around the 540 nm to 700 nm wavelength range that are subtracted from the intensities of the cornea with Riboflavin. Intensity profiles of Riboflavin corneas minus the baseline are then fitted using a solution to Fick's second law of diffusion equation:

$$C = C_0\left(1 - \operatorname{erf}\left(\frac{x}{2\sqrt{Dt}}\right)\right) \quad \text{Eq. 1}$$

where C is concentration in the medium diffused, $C_0$ is initial concentration at boundary, x is spatial distance, D is the diffusion coefficient and t is time between application and observation (i.e., the time for diffusion).

Because the intensity of fluorescence is approximately proportional to the concentration of Riboflavin through the cornea, the diffusion equation can be approximately transformed in terms of observed fluorescence intensity. The observed fluorescence intensity is the intensity observed after instillation less the background intensity observed prior to instillation (i.e., the fluorescent images less the background). Thus, in the approximation that observed intensity, I, is proportional to concentration, C, the diffusion equation is transformed to:

$$I = I_0\left(1 - \operatorname{erf}\left(\frac{x}{2\sqrt{Dt}}\right)\right) \quad \text{Eq. 2}$$

where I is intensity across the cross-section of the cornea, and $I_0$ is initial intensity at the boundary (i.e., the corneal surface) and x, D and t are the same as in Eq. 1.

Figure 12:
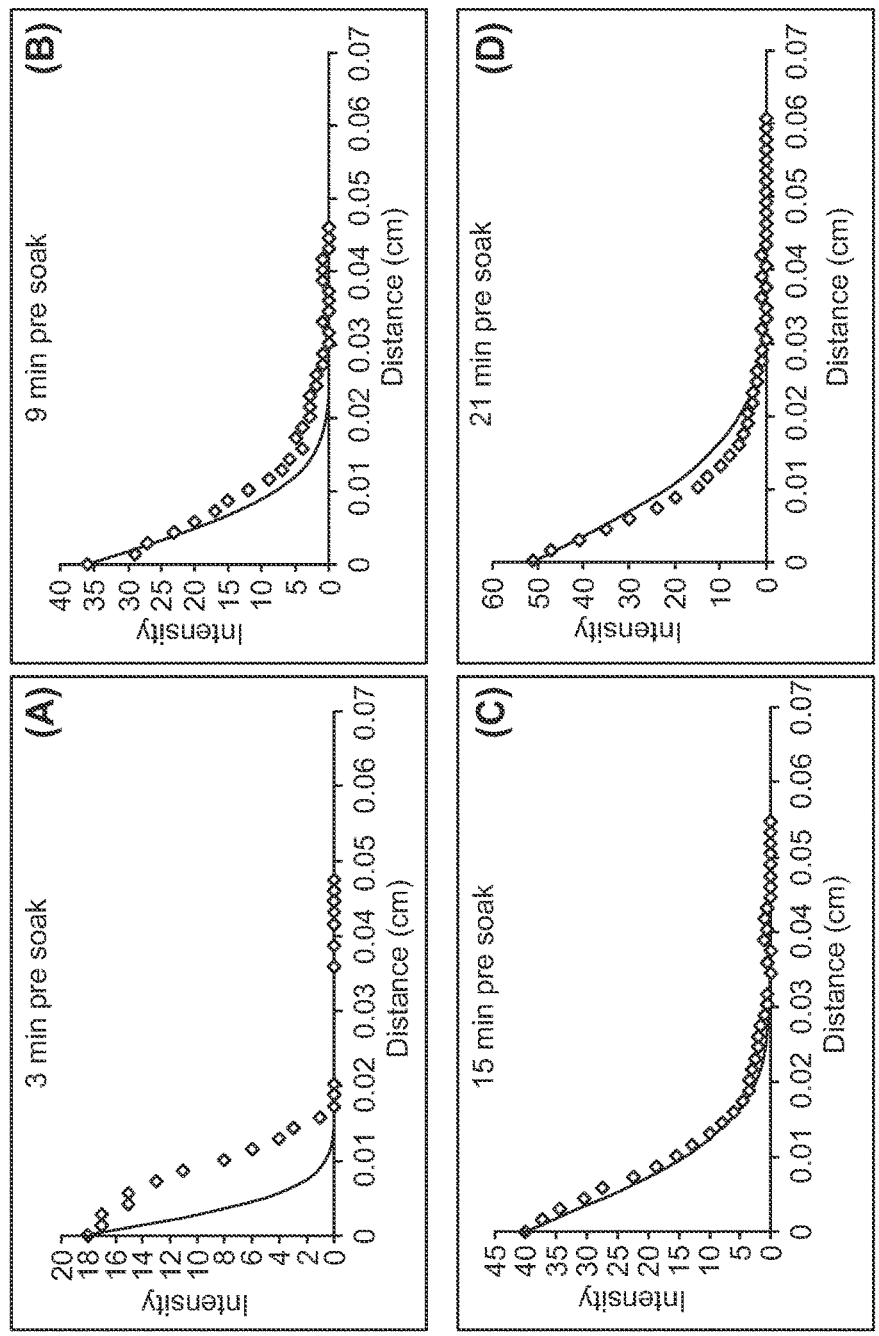
FIG. 12 illustrates the results of a procedure to extract the concentration of Riboflavin as a function of distance within the eye at different pre-soak durations.

FIG. 12 shows the data and their respective best-fit curve to Eq. 2. All four curve fits were done using a value of $2.5\times10^{-7}$ cm$^2$/s for the diffusion coefficient, D. Apart from the 3 minute pre-soak time shown in quadrant (a), the curve fits are all very close to the actual data giving confidence in the values selected for the diffusion coefficient. Quadrants (b), (c), and (d), illustrate the results for the 9 minute, 15 minute, and 22 minute pre-soak times.

Figure 13:
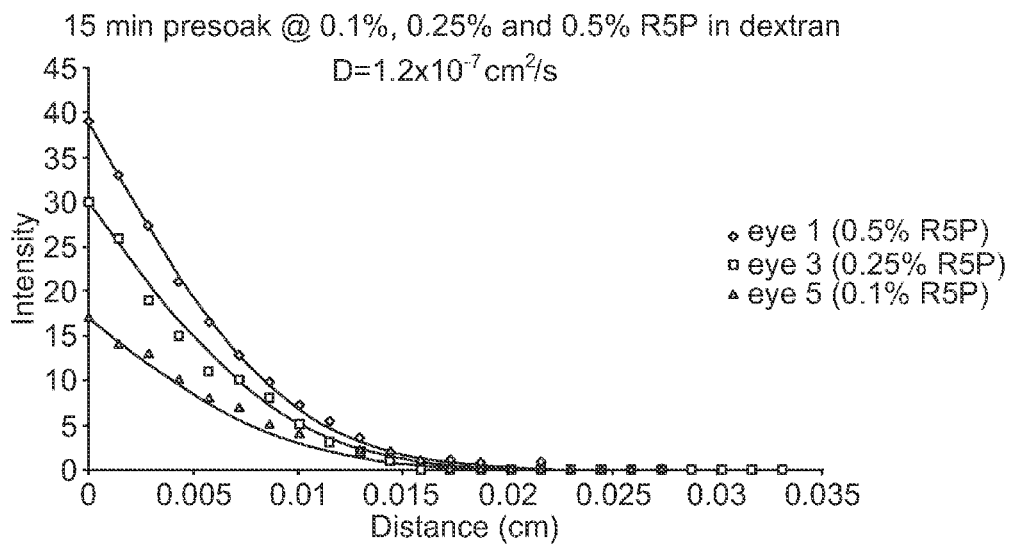
FIG. 13 illustrates the results of a procedure to extract the concentration of Riboflavin as a function of distance within the eye at different Riboflavin concentrations.

During the second part of the experiment, data from various Riboflavin-5-phosphate concentrations was treated to a similar analysis. As shown in FIG. 13, a curve fit to the solution of the diffusion equation was applied for each concentration of Riboflavin. For a constant 15 minute pre-soak without any interruption, the diffusion coefficient that fit all three curves was $1.2\times10^{-7}$ cm$^2$/s.

Figure 14:
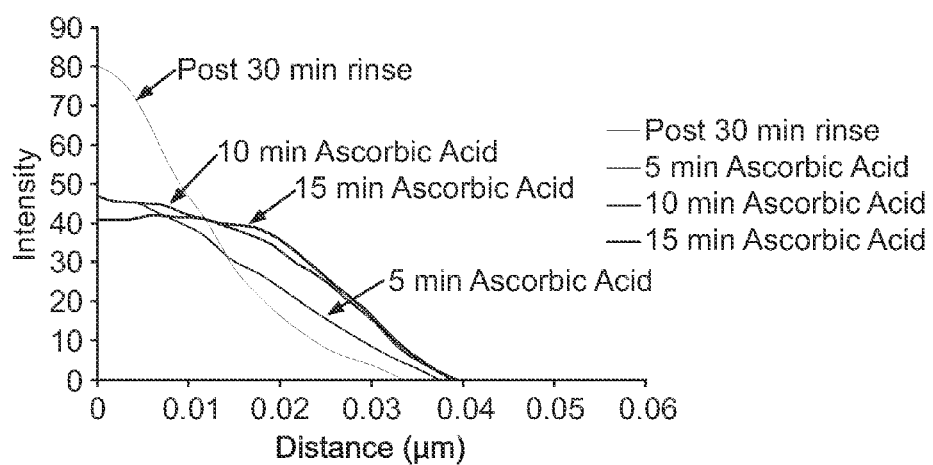
FIG. 14 illustrates the observed fluorescence intensity as a function of depth within the eye for varying applications of the quenching agent.
Figure 15A:
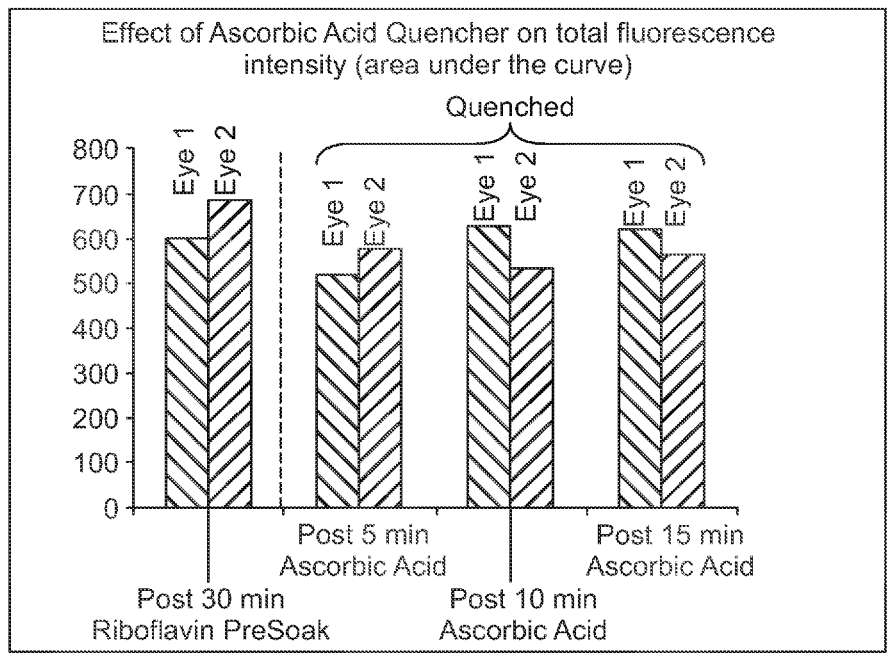
FIG. 15A illustrates the total (cumulative) intensity observed for both sample eye 1 and sample eye 2 after applying the quenching agent for varying durations.
Figure 15B:
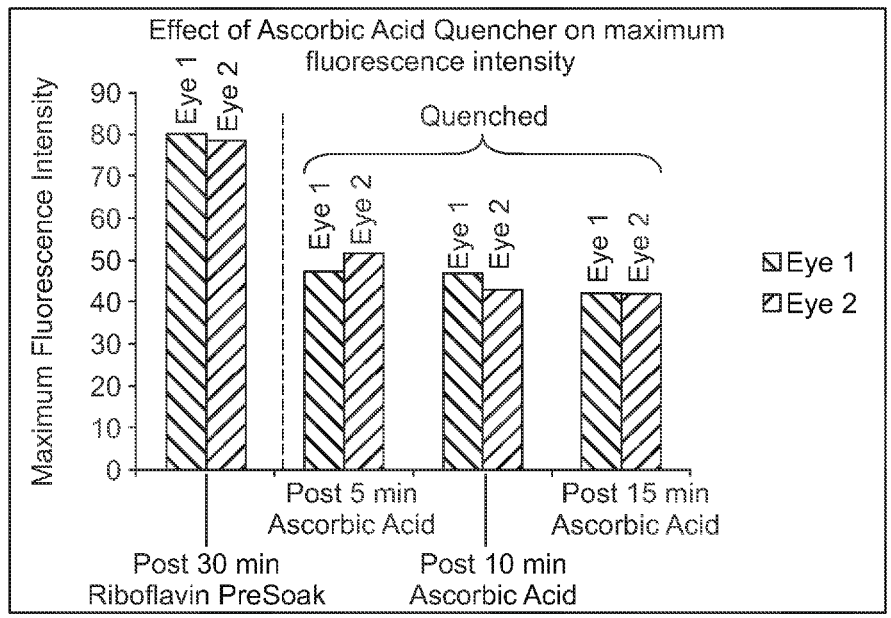
FIG. 15B illustrates the maximum intensity observed for both sample eyes after applying the quenching agent for varying durations.

Soaking the eye with the ascorbic acid considerably decreases the maximum fluorescence intensity observed with the Scheimpflug imager as shown in the FIGS. 14, 15A, and 15B. FIG. 14 provides four curves illustrating the observed intensity as a function of depth within the eye for varying applications of the quenching agent. FIG. 15A illustrates the total (cumulative) intensity observed at all depths of the eye for both sample eye 1 and sample eye 2 at varying durations of the quenching agent. FIG. 15B illustrates the maximum intensity observed for both sample eyes at varying durations of the quenching agent. In FIGS. 14, 15A, and 15B, results are shown for the sample eyes in four states: after a 30 minute pre-soak in Riboflavin, but prior to application of the quenching agent; following the 30 minute pre-soak in Riboflavin, and following a 5 minute application of the quenching agent; following the 30 minute pre-soak in Riboflavin, following a 10 minute application of the quenching agent; following the 30 minute pre-soak in Riboflavin, and following a 15 minute application of the quenching agent. As shown in FIGS. 14 and 15B, the maximum intensity, and thus the maximum concentration of Riboflavin, was observed for the sample eyes prior to the application of the quenching agent. This confirms the utility of ascorbic acid as a fluorescence quencher. FIGS. 15A and 15B illustrate the drop in fluorescence intensity after five, ten and fifteen minutes of ascorbic acid pre-soak after pre soaking with Riboflavin for 30 min. FIG. 14 also illustrates that the observed intensity is increased at greater depths within the eye following the application of the quenching agent. This effect can be due to further diffusion (i.e., penetration) of the Riboflavin into the corneal tissue prior to the quenching agent inhibiting the fluorescence of the Riboflavin, or can be due to other fluorescent substances within the eye, such as substances resulting from the degradation of the Riboflavin.

Figure 16A:
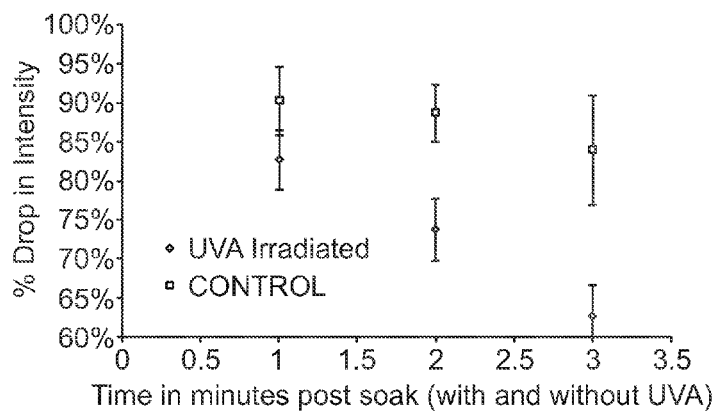
FIG. 16A illustrates results comparing the maximum intensity observed in an eye after applying UVA to the eye for varying durations and compared with a control eye.
Figure 16B:
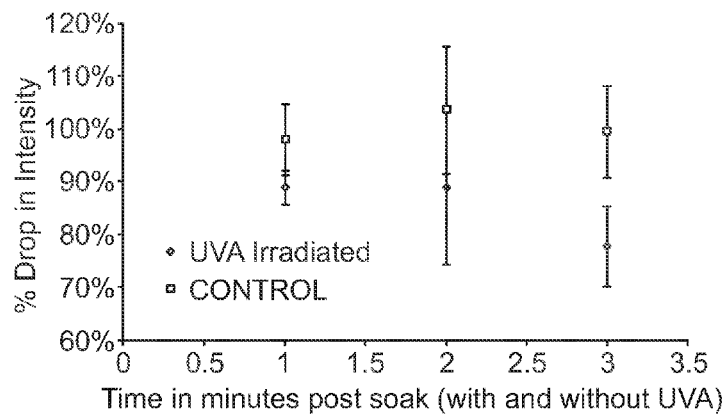
FIG. 16B illustrates results comparing the total cumulative intensity observed in an eye after applying UVA to the eye for varying durations and compared with a control eye.

As shown in FIGS. 16A and 16B, the effect of UVA irradiation decreases the fluorescence of the Riboflavin in the cornea. Longer irradiation has a greater effect on the fluorescence loss of the Riboflavin in the cornea. This loss is the result of the UVA and not simple diffusion of Riboflavin through the cornea as shown by the control eyes. The two graphs show the drop in maximum fluorescence detected (FIG. 16A) as well as the total fluorescence in the cornea that could be calculated from the area under the intensity profile curve (FIG. 16B). As shown in FIG. 16A, the drop in maximum fluorescence intensity was detected after 1, 2 and 3 minutes of UVA irradiation (no UVA for control eyes) after pre soaking with Riboflavin for 30 min. Fluorescence decreases with higher irradiating energy. As shown in FIG. 16B, the drop in total fluorescence intensity was detected after one, two and three minutes of UVA irradiation (no UVA for control eyes) after pre soaking with Riboflavin for 30 min. Total cumulative intensity of fluorescence, which approximates the total distributed Riboflavin throughout the cornea, was calculated by finding the area under the intensity curve.

This initial proof of concept work shows the feasibility of using a Scheimpflug imaging system and analyzer combined with a filter to detect the diffusion and distribution of Riboflavin in corneal tissue based on the fluorescence of photo-activated Riboflavin. As described herein in connection with FIG. 9, such systems can be combined with a cross-linking activation and monitoring system to advantageously provide real-time monitoring of the distribution ("diffusion") of a cross-linking agent within corneal tissue prior to, or during, initiation of cross-linking.

According to aspects of the present disclosure provide systems and methods for monitoring time based photo active agent delivery or photo active marker presence. Aspects further provide systems and methods for measuring the effects of conducting eye therapy, especially when a cross-linking agent is applied to stabilize desired shape changes generated in corneal tissue.

The fluorescence dosimetry system consists of a Scheimpflug optical system configured to take cross sectional images of the eye before and during instillation of a cross-linking agent to monitor the tissue uptake and drug concentration as a function of depth and/or position within the corneal tissue. In addition, a slit lamp configuration can be utilized to provide cross sectional images of the eye. It may also be used during and after the photo activating cross-linking procedure for real-time monitoring of the concentration and consumption of the cross-linking agent monitoring the amount of cross-linking achieved.

Several commercial ophthalmic Scheimpflug image capture systems are commercially available. These include the Pentacam corneal topography system made by Oculus http://www.pentacam.com/sites/messprinzip.php as well as the GALILEI and GALILEI G2 corneal topography systems made by Ziemer Group http://www.ziemergroup.com/products/g2-main.html.

The Scheimpflug systems generally provide a slit of light for illumination at the fluorescence excitation wavelengths of the cross-linking agent. This causes fluorescence emission of the cross-linking agent which is proportional to the cross-linking agent concentration within the target tissue. By periodically monitoring the cross-linking agent over time one can precisely determine the depth and concentration of the cross-linking agent within the tissue both spatially and temporally. This allows for tailored drug delivery for individual patients since drug uptake may be different based on their own particular physiology.

Scheimpflug imaging differs from conventional techniques in that the object plane, lens plane, and image plane are not parallel to each other. Instead, the three planes intersect in a line. The advantage of the Scheimpflug geometry is that a relatively greater depth of focus is achieved that is available in typical optical arrangements. The Scheimpflug principle has been applied in ophthalmology to obtain optical sections of the entire anterior segment of the eye, from the anterior surface of the cornea to the posterior surface of the lens. This type of imaging allows assessment of anterior and posterior corneal topography, anterior chamber depth, as well as anterior and posterior topography of the lens.

Figure 17A:
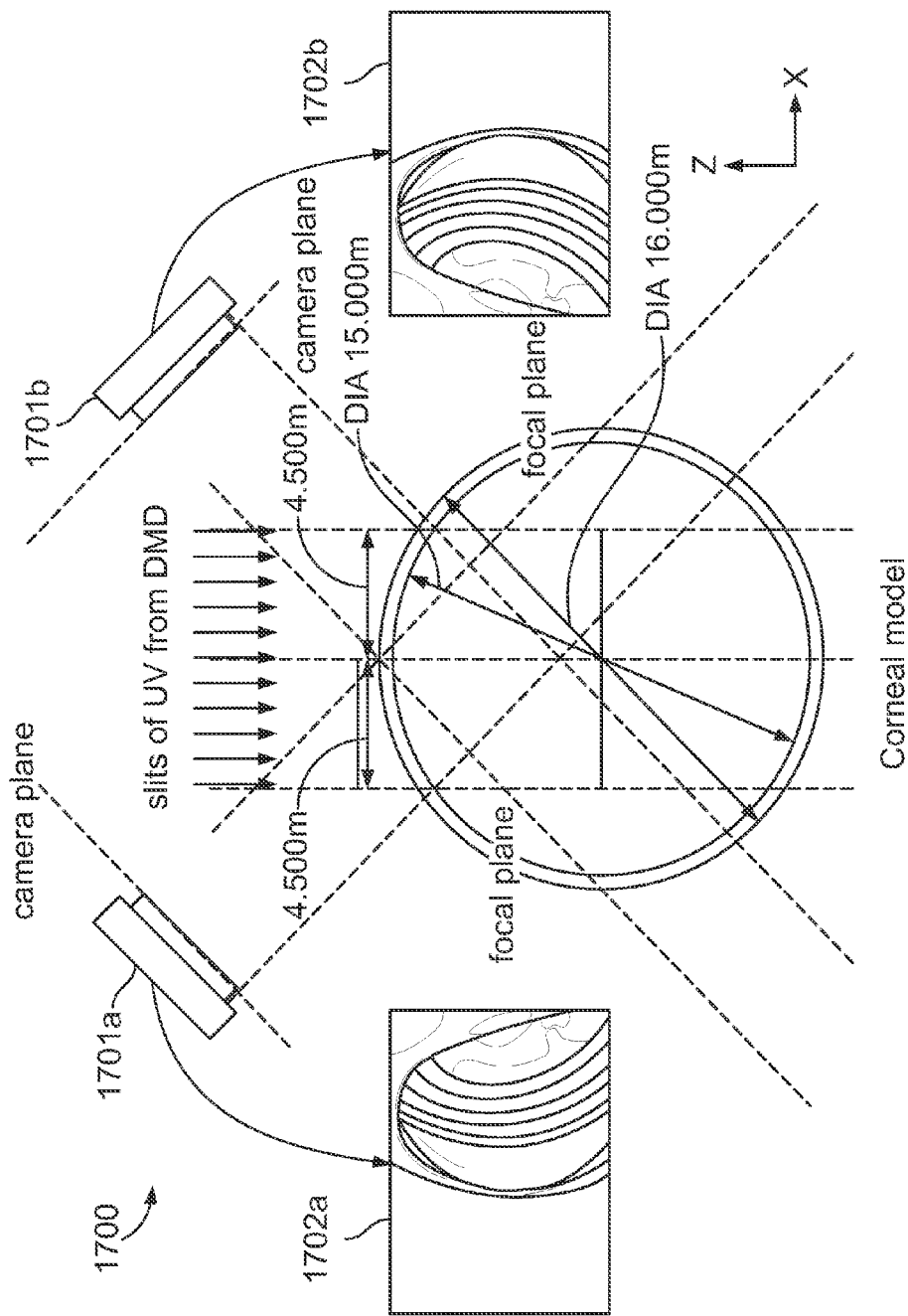
FIG. 17A illustrates an example system for measuring the intensity of the Riboflavin florescence in profile through the cornea.

Referring to FIG. 17A, an example system 1700 measures the intensity of the Riboflavin fluorescence in profile through the cornea. The system 1700 may be implemented to estimate Riboflavin concentrations in the treatment zone prior to and during treatment. In the corneal model of FIG. 17A, the radius of curvature of the cornea is approximately 8 mm and the corneal thickness is approximately 0.5 mm.

As shown in FIG. 17A, the system 1700 employs two off-axis cameras 1701*a*, 1701*b* to capture images of a cornea illuminated by slits of UV light. The illumination source may include a DMD system to selectively direct the light to the corneal tissue as slits of light. Alternatively, the illumination source may include a multiple line generator using an optical grating or a scanning mirror system to selectively direct the light to the corneal tissue as the slits of light. The slits of UV light illuminate a treatment zone on the cornea having a diameter of 9 mm. With the slit illumination, the camera 1701*a* captures a cross-sectioned image 1702*a* for half of the 9 mm treatment area (a 4.5 mm section). Meanwhile, the camera 1701*b* captures a cross-sectioned image 1702*b* for the other half of the 9 mm treatment area (a 4.5 mm section).

Figure 17B:
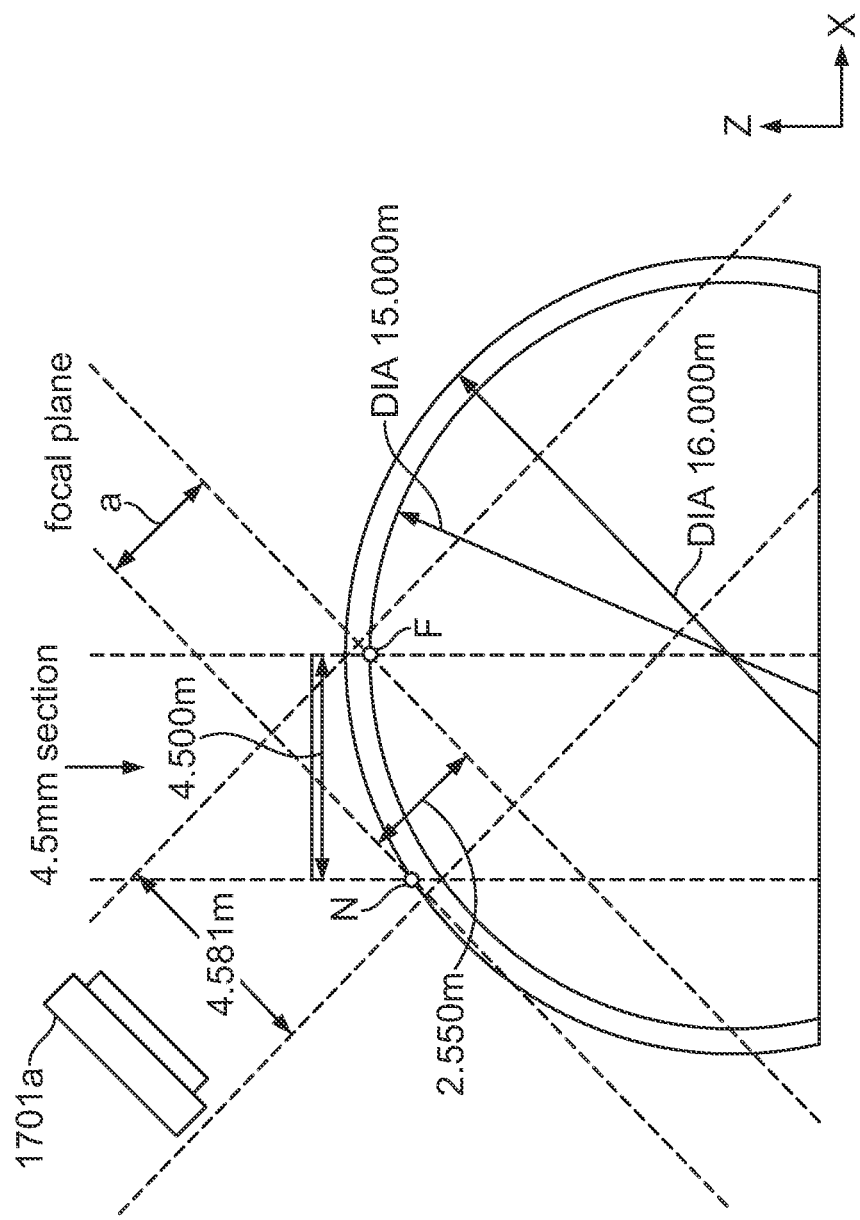
FIG. 17B illustrates a focal plane range for the example system of FIG. 17A.

The image planes of both cameras 1701*a, b* ("camera plane") are each aligned approximately 45° from the axis defined by the UV illumination, i.e., the z-axis. The focal planes for both cameras 1701*a, b* are parallel to the camera planes. As shown in FIG. 17B, to capture the profile for a corneal thickness of 0.5 mm for the 4.5 mm section, the depth of focus associated with the focal plane of the camera 1701*a* spans a range a, e.g., 2.55 mm. In other words, the range a allows the camera 1701*a* to capture image data from the nearest point N of the cornea (at top of cornea) and the farthest point F of the cornea (at bottom of cornea) relative to the camera 1701*a*, within the 4.5 mm section. Although not shown in FIG. 17B, the camera 1701*b* is similarly configured on the opposing side of the axis.

Figure 18A:
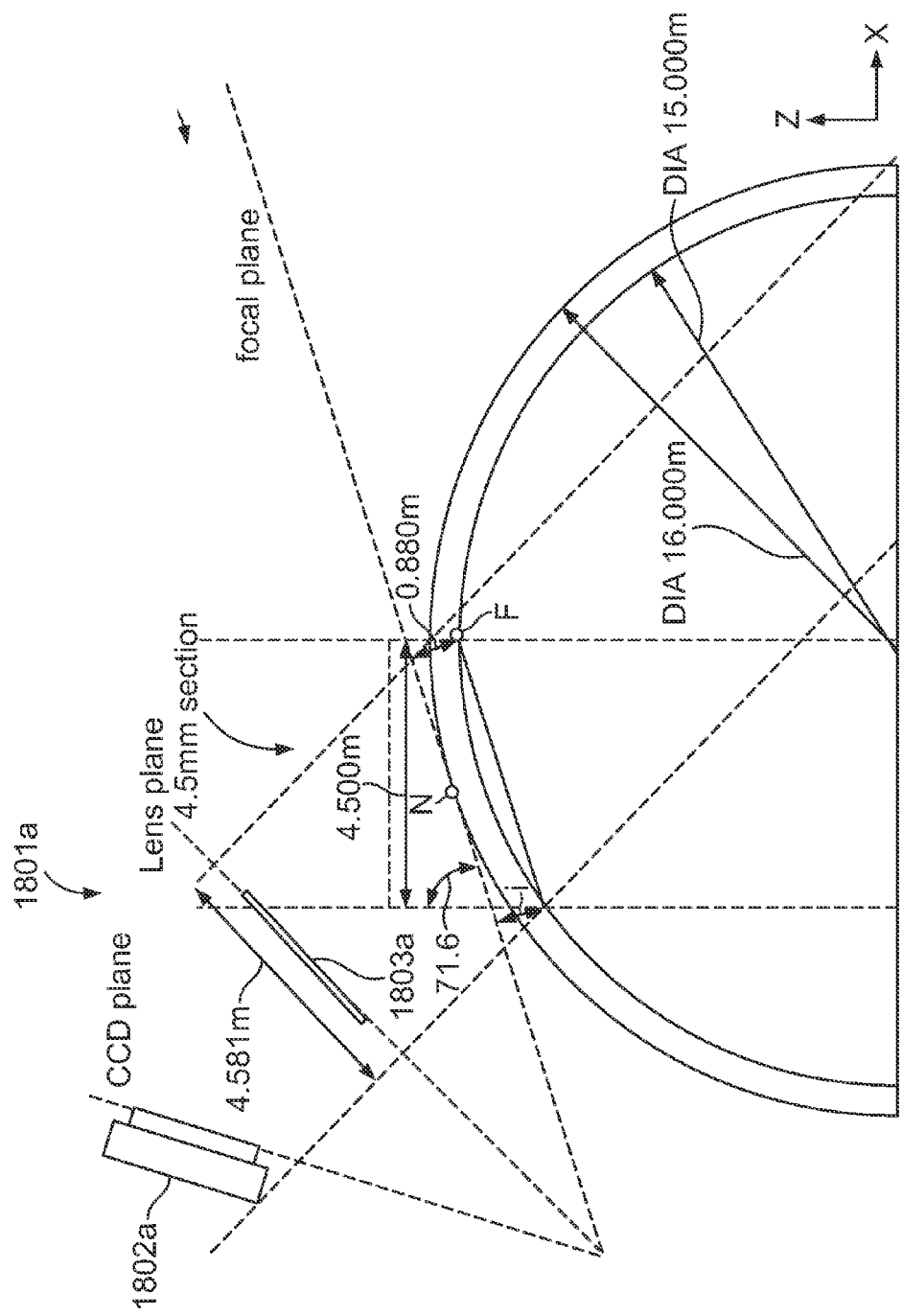
FIG. 18A illustrates another example system for measuring the intensity of the Riboflavin florescence in profile through the cornea.

Referring to FIG. 18A, another example system 1800 measures the intensity of the Riboflavin florescence in profile through the cornea. The system 1800 employs two off-axis Scheimpflug systems to capture images of a cornea illuminated by slits of UV light controlled, for example, by a DMD system. Although only one Scheimpflug system 1801*a* is illustrated for simplicity, it is understood that another Scheimpflug system is similarly employed. Like the corneal model of FIG. 17A, the radius of curvature of the cornea is approximately 8 mm and the corneal thickness is approximately 0.5 mm. The slits of UV light also illuminate a treatment zone on the cornea having a diameter of 9 mm. With the slit illumination, the Scheimpflug system 1801*a* captures a cross-sectioned image for half of the 9 mm treatment area (a 4.5 mm section). Meanwhile, the second Scheimpflug system captures a cross-sectioned image for the other half of the 9 mm treatment area (a 4.5 mm section).

The Scheimpflug system 1801*a* includes a CCD camera 1802*a* and a lens 1803*a*. The plane of the CCD camera 1802*a* ("CCD plane") is aligned approximately 18.4° from the axis defined by the UV illumination, i.e., the z-axis. Meanwhile, the plane of the lens 1803*a* ("lens plane") is aligned 45° from the axis. As shown in FIG. 18A, the CCD plane, the lens plane, and the focal plane intersect at a common line.

To capture the profile for a corneal thickness of 0.5 mm for the 4.5 mm section, the depth of focus associated with the focal plane of the CCD camera 1802*a* spans over a range i, e.g., 0.88 mm. In other words, the range i allows the camera 1802*a* to capture image data from the nearest point N of the cornea (on anterior surface) and the farthest point F of the cornea (on posterior surface) relative to the Scheimpflug system 1801*a*, within the 4.5 mm section. Compared to the system 1700 described previously, a smaller range for the depth of focus is required for the system 1800 to capture the corneal profile.

Figure 17D:
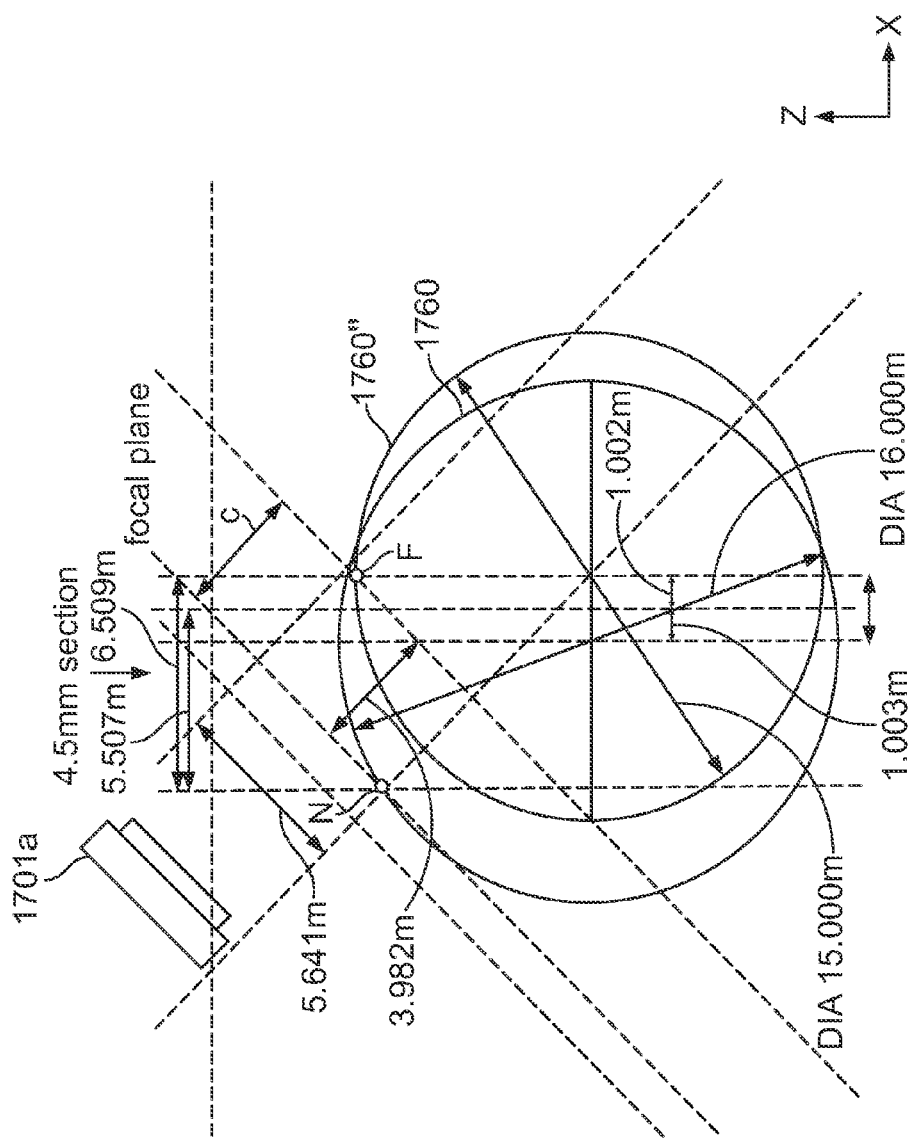
FIG. 17D illustrates a focal plane range for the example system of FIG. 17A based on movement of the eye along another axis.
Figure 18B:
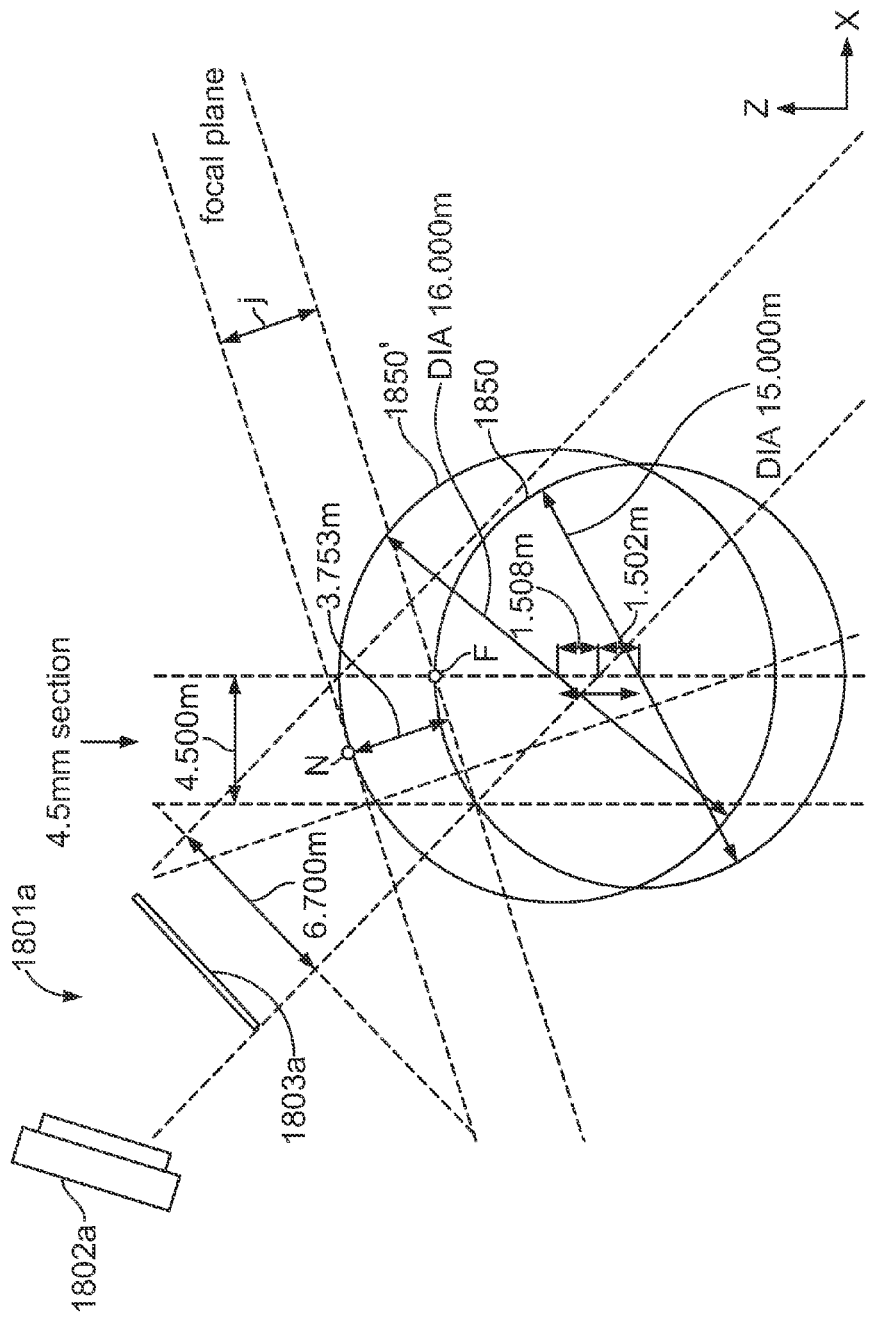
FIG. 18B illustrates a focal plane range for the example system of FIG. 18A based on movement of the eye along an axis.

As shown in FIGS. 17C, 17D, 18B, and 18C, the range for the depth of focus may need to be greater to accommodate possible movement of the eye, e.g., along the x-axis or z-axis. Because the eye may move in a clinical environment, monitoring systems must be sufficiently robust to account for such movement. In particular, FIGS. 17C and 18B show possible movement of the eye of +/−1.5 mm along the z-axis. As shown in FIG. 17C, the boundary 1750 reflects the position of the bottom surface of the cornea after the eye moves −1.5 mm along the z-axis, and the boundary 1750' reflects the position of the surface of the cornea after the eye moves +1.5 mm along the z-axis. The boundaries 1750 and 1750' include, respectively, the farthest point F and the nearest point N for the cornea relative to the camera 1701*a* as the eye moves along the z-axis. To capture the profile for a corneal thickness of 0.5 mm for the 4.5 mm section when the eye moves +/−1.5 mm along the z-axis, FIG. 17C shows that the system 1700 has a depth of focus perpendicular to the focal plane and spanning a total range b, i.e., approximately 4.68 mm, to simultaneously capture the nearest point N and the furthest point F.

Similarly, in FIG. 18B, the boundary 1850 reflects the position of the bottom surface of the cornea after the eye moves −1.5 mm along the z-axis, and the boundary 1850' reflects the position of the top surface of the cornea after the eye moves +1.5 mm along the z-axis. The boundaries 1850 and 1850' include, respectively, the farthest point F and the nearest point N for the cornea relative to the Scheimpflug system 1801*a*, as the eye moves along the z-axis. To capture the profile for a corneal thickness of 0.5 mm for the 4.5 mm section when the eye moves +/−1.5 mm along the z-axis, FIG. 18B shows that the system 1800 has a depth of focus that spans a total range j, i.e., approximately 3.75 mm. Compared to the system 1700, the system 1800 requires a smaller range for the depth of focus to accommodate the same possible movement of the eye along the z-axis.

Figure 18C:
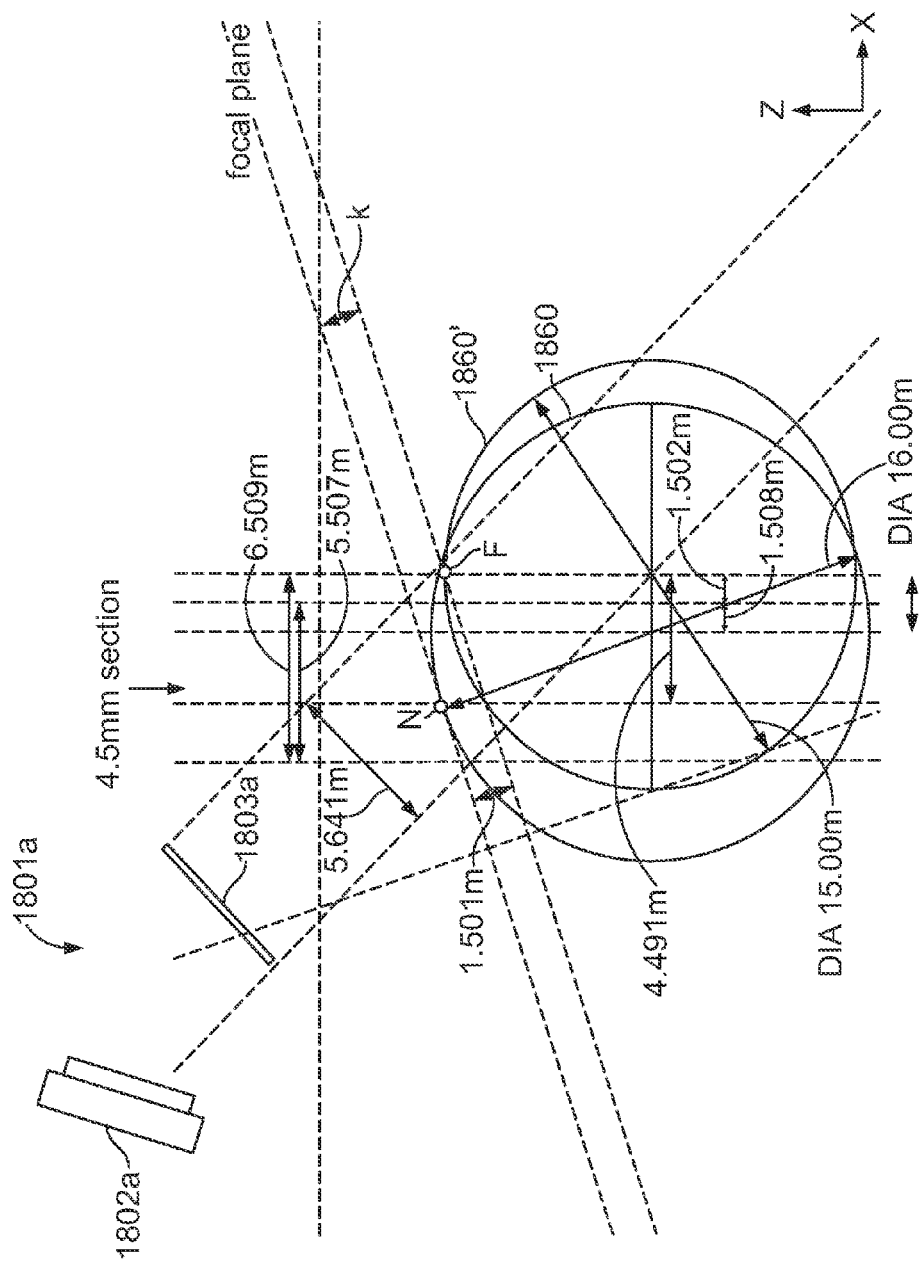
FIG. 18C illustrates a focal plane range for the example system of FIG. 18A based on movement of the eye along another axis.

FIGS. 17D and 18C show possible movement of the eye of +/−1.0 mm along the x-axis. As shown in FIG. 17D, the boundary 1760 reflects the position of the top surface of the cornea after the eye moves −1.0 mm along the x-axis, and the boundary 1760' reflects the position of the bottom surface of the cornea after the eye moves +1.0 mm along the x-axis. With such movement, the 4.5 mm section also moves. The boundaries 1760 and 1760', respectively, include the nearest point N and the farthest point F for the cornea relative to the camera 1701*a*, as the eye moves from along the x-axis. To capture the profile for a corneal thickness of 0.5 mm for the 4.5 mm section when the eye moves +/−1.0 mm along the x-axis, FIG. 17D shows that the system 1700 has a depth of focus that spans a total range c, i.e., approximately 3.98 mm.

Similarly, in FIG. 18C, the boundary 1860 reflects the position of the top surface of the cornea after the eye moves −1.0 mm along the x-axis, and the boundary 1860' reflects the position of the bottom surface of the cornea after the eye moves +1.0 mm along the x-axis. With such movement, the 4.5 mm section also moves. The boundaries 1860 and 1860', respectively, include the nearest point N and the farthest point F for the cornea relative to the Scheimpflug system 1801*a*, as the eye moves from along the x-axis. To capture the profile for a corneal thickness of 0.5 mm for the 4.5 mm section when the eye moves +/−1.0 mm along the x-axis, FIG. 18C shows that the system 1800 has a depth of focus that spans a total range k, i.e., approximately 1.5 mm. Again compared to the system 1700, the system 1800 requires a smaller range for the depth of focus to accommodate the same movement of the eye along the x-axis.

Advantageously, the range for the depth of focus in the system 1800 is smaller distance than the range for the system 1700 to capture the corneal profile. In particular, for a given shift in eye position, the depth of focus required by the system 1800 is smaller than the depth of focus required by the system 1700 to continue to observe a both the posterior and anterior surfaces of a 4.5 mm section of the cornea. As such, for a given depth of focus, the system 1800 is less sensitive to movement of the eye and may be more robust than the system 1700 in a clinical environment.

While the angle of the CCD camera in the example system 1800 may be 18.4°, a system employing a similar configuration of two off-axis Scheimpflug systems to capture the corneal fiber may employ other camera angles which can be selected to minimize the required range for the depth of focus in the optics employed. As shown in FIGS. 18A-C, the optimal angle is determined at least by the dimensions of the treatment area, the radius of curvature of the cornea, and the corneal thickness. Some embodiments may apply the Scheimpflug principle employing a range of camera angles of approximately 5 to approximately 85 degrees and approximately −5 to approximately 85 degrees. In some examples, the optical elements can be arranged such that the focal plane is approximately tangentially co-planar with a point of the corneal surface at the center of the section of interest (e.g., the 4.5 mm sections described in connection with FIGS. 17-18).

While the system 1800 is described with two Scheimpflug systems, aspects of the present disclosure apply to systems with one off-axis Scheimpflug system. Additionally or alternatively one or more of such Scheimpflug systems may rotate (for example about an axis generally parallel to the corneal optical axis so as to capture indications of concentrations of photo-active substances from additional portions of the cornea.

While particular angular orientations and dimensions are provided in describing the example system 1800 for exemplary and descriptive purposes, such Scheimpflug imaging systems are generally arranged so as to minimize the requirements of the depth of focus of the Scheimpflug imaging system, particular under conditions where the position of the cornea may change dynamically during measurement (such as in a clinical environment). Minimization of the depth of focus requirements is generally achieved by at least approximately aligning the focal plane of the Scheimpflug imaging system to be generally tangential to the corneal boundary at a mid-point of the corneal surface being imaged (as illustrated by the point N in FIG. 18A roughly bisecting the 4.5 mm imaging region and located such that the focal plane is approximately co-planar with the surface of the cornea at point N). In a particular embodiment of the Scheimpflug imaging system (where imaging regions may be more or less than 4.5 mm), the orientations of the CCD plane and lens plane can be selected so as to allow a focal plane to be generally tangential with at least a portion of the corneal surface in the region being imaged. In some embodiments, the focal plane is generally tangential with a central region (e.g., a mid-point) of the region being imaged.

Furthermore, some aspects of the present disclosure provide a Scheimpflug imaging system where the intersection of the CCD plane, lens plane, and focal plane is located generally below an upper-most surface of the cornea being imaged. For example, as shown in FIG. 18A, the point of intersection is located below (i.e., in a negative z-direction) the uppermost portion of the cornea (i.e., the most positive z-direction position of the cornea). Orienting the Scheimpflug imaging system with a point of intersection generally below the uppermost region of the cornea generally allows the focal plane to be tangential with portions of the eye being imaged, rather than focal planes which are oriented generally perpendicularly to the corneal surface so as to provide cross-sectional views thereof.

The rate at which a particular fluorescing marker is taken up by the tissue may also be an indicator of different pathologies of disease. The mere presence of a particular fluorescing marker taken up by the tissue may also be an indicator of different pathologies of disease. Alternatively, the rate at which a particular fluorescing marker is taken up by the tissue may also be an indicator of different biochemical, bio-mechanical, or opto-mechanical properties of the tissue.

Utilizing various combinations of fluorescence excitation wavelengths and fluorescence emission collecting filters, one can tailor the system to monitor many different photoactive agents and markers.

The systems described herein (e.g., the system 1000*a* of FIG. 10A) may also be used to differentiate patients who have slow versus fast diffusion rates so as to determine the best time of light treatment post instillation of drug delivery. For example, for a transepithelial Riboflavin solution, the thickness and health of a patient's epithelium directly relates to the diffusion rate and thereby the concentration of Riboflavin at a given depth within the cornea. The diffusion rates of the epithelium and the underlying stroma are different. Knowing this information as well as the thickness of the epithelium and stroma of the cornea, allows for better control of the cross-linking process because of biological variation between individual patients.

For example, the average soak time for drug delivery might be 10 minutes for a given formulation of Riboflavin. Measuring an individual patient with the system at 4 minutes may allow for a predicted drug delivery concentration at 8 minutes, 10 minutes or 12 minutes based on that individual's diffusion rate.

This can also be useful for understanding the diffusion rates of transepithelial Riboflavin delivery for patients with different disease states such as keratoconus. In keratoconus the cornea becomes weakened and the cornea bulges creating cone like structures. These structures often have different epithelial thicknesses and epithelial health than the rest of the cornea. By understanding the rate and/or concentration of drug delivery below these structures delivery of proper treatment may be obtained.

This system could also be utilized to understand when to place a quencher on the surface of the cornea after drug delivery to help protect the epithelium and allow for better depth penetration of photons into the cornea. The quencher is thereby acting as an optical clearing agent for the epithelium. This effect can be seen, for example, in the example results described above in connection with FIGS. 14, 15A, and 15B.

The system can be used during UVA illumination to monitor the Riboflavin quenching and depletion as a function of time. The monitored Riboflavin distributions can be correlated to the amount of cross-linking and clinical outcomes to better understand differences between attempted clinical outcomes and actually achieved clinical outcomes. In this way the system could be used to determine the specific amount of UVA dose to achieve a specific outcome for an individual with a given diffusion rate and cross-linking profile. The UVA dose could be stopped at certain intervals and quickly monitored by the fluorescence dosimetry system (e.g., the system 500 having a Scheimpflug optical system or the system 600 having a slit lamp). For example, a sample can be made periodically every ten seconds for a duration of 100 milliseconds (e.g., the average of three slit lamp images at 30 fps frame rate).

The use of Riboflavin as the cross-linking agent and UV light as the initiating element in the embodiments above is described for illustrative purposes only. In general, other types of cross-linking agents may be alternatively or additionally employed according to aspects of the present disclosure. Thus, for example Rose Bengal (4,5,6,7-tetrachloro-2',4',5',7'-tetraiodofluorescein) may be employed as the cross-linking agent 130, or as the cross-linking agent delivered in varying concentrations 912, 1022. Rose Bengal has been approved for application to the eye as a stain to identify damage to conjunctival and corneal cells. However, Rose Bengal can also initiate cross-linking activity within corneal collagen to stabilize the corneal tissue and improve its biomechanical strength. Like Riboflavin, photo-activating light may be applied to initiate cross-linking activity by causing the Rose Bengal to convert $O_2$ in the corneal tissue into singlet oxygen. The photo-activating light may include, for example, UV light or green light. The photo-activating light may include photons having energy levels sufficient to individually convert $O_2$ into singlet oxygen, or may include photons having energy levels sufficient to convert $O_2$ into singlet oxygen in combination with other photons, or any combination thereof.

Although embodiments of the present disclosure may describe stabilizing corneal structure after treatments, such as LASIK surgery and thermokeratoplasty, it is understood that aspects of the present disclosure are applicable in any context where it is advantageous to form a stable three-dimensional structure of corneal tissue through cross-linking. Furthermore, while aspects of the present disclosure are described in connection with the re-shaping and/or strengthening of corneal tissue via cross-linking the corneal collagen fibrils, it is specifically noted that the present disclosure is not limited to cross-linking corneal tissue, or even cross-linking of tissue. Aspects of the present disclosure apply generally to the controlled cross-linking of fibrous matter and optionally according to feedback information. The fibrous matter can be collagen fibrils such as found in tissue or can be another organic or inorganic material that is arranged, microscopically, as a plurality of fibrils with the ability to be reshaped by generating cross-links between the fibrils. Similarly, the present disclosure is not limited to a particular type of cross-linking agent or initiating element, and it is understood that suitable cross-linking agents and initiating elements can be selected according to the particular fibrous material being reshaped and/or strengthened by cross-linking.

In some embodiments, for example, the cross-linking agent may be Riboflavin and the initiating element may be photo-activating light, such as ultraviolet (UV) light. In these embodiments, the photo-activating light initiates cross-linking activity by irradiating the applied cross-linking agent to generate reactive radicals in the corneal tissue.

The present disclosure includes systems having controllers for providing various functionality to process information and determine results based on inputs. Generally, the controllers (such as the controller 120 described throughout the present disclosure) may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller 120 may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present disclosure, as is appreciated by those skilled in the computer and software arts. The physical processors and/or machines may be externally networked with the image capture device(s) (e.g., the camera 760, or cameras 1051, 1052, etc), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described in connection with a number of exemplary embodiments, and implementations, the present disclosure is not so limited, but rather cover various modifications, and equivalent arrangements.

What is claimed is:

1. A system for monitoring treatment of corneal tissue, comprising:
    an excitation source that directs light to the corneal tissue treated with a cross-linking agent, the light causing the cross-linking agent to fluoresce;
    an image capture system that captures one or more images of the corneal tissue in response to the excitation source directing the light to the corneal tissue, the one or more images showing the fluorescing cross-linking agent; and
    a controller that is configured to receive the one or more images of the corneal tissue and to provide information relating to cross-linking activity with the cross-linking agent in the corneal tissue based on one or more wavelengths emitted by the fluorescing cross-linking agent,
    wherein the excitation source directs the light to the corneal tissue along an axis; the image capture system includes a camera and a lens; the camera captures the one or more images of the corneal tissue via the lens; the camera and the lens are offset from the axis defined by the light; the camera defines an image plane; the lens defines a lens plane; the lens plane is separate from the image plane; the one or more images of the corneal tissue are associated with a focal plane defined by the camera and the lens; and the camera and the lens are oriented such that the image plane, the lens plane, and the focal plane all intersect each other at a common intersection.

2. The system of claim 1, wherein the excitation source directs the light to the corneal tissue as one or more slits of light, and the camera that captures the one or more images of the corneal tissue defined by the one or more slits of light.

3. The system of claim 2, wherein the excitation source includes a multiple line generator using an optical grating or a mirror system to selectively direct the light to the corneal tissue as the more than one slits of light.

4. The system of claim 1, wherein the excitation source includes a digital micro-mirror device (DMD) to selectively direct the light to the corneal tissue.

5. The system of claim 1, wherein the focal plane is approximately parallel to a plane that is tangent to an apex of a corneal surface that corresponds to being captured by the camera.

6. The system of claim 1, wherein the excitation source and the image capture system rotate about the corneal tissue to capture a plurality of cross-sectional images of the corneal tissue.

7. The system of claim 1, wherein the controller determines an intensity of the fluorescing cross-linking agent in the more than one image captured over a period of time, and changes in the intensity of the fluorescing cross-linking agent reflect an amount of cross-linking activity generated by activation of the cross-linking agent over the period of time.

8. The system of claim 1, wherein the excitation source includes a plurality of slit lamps arranged about the corneal tissue, the image capture system capturing the one or more images of the corneal tissue in response to the plurality of slit lamps directing the light to the corneal tissue.

9. The system of claim 1, wherein the excitation source directs the light to the corneal tissue as a slit at an incident angle in a range from approximately 20 degrees to approximately 70 degrees relative to the image capture system.

10. The system of claim 1, wherein each of the one or more images of the corneal tissue provides a cross-sectional image, and the controller is configured to provide information relating to cross-linking activity at varying depths of the corneal tissue.

11. The system of claim 1, further comprising an applicator configured to apply additional cross-linking agent and generate additional cross-linking activity in response to the information relating to the cross-linking activity.

12. The system of claim 1, further comprising a photo-activating system configured to apply additional light to activate the cross-linking agent further and generate additional cross-linking activity in response to the information relating to the cross-linking activity.

13. The system of claim 1, wherein the light from the excitation source activates the cross-linking agent to generate the cross-linking activity.

14. The system of claim 13, wherein the excitation source is configured to apply additional light to activate the cross-linking agent further and generate additional cross-linking activity in response to the information relating to the cross-linking activity.

15. The system of claim 1, wherein the controller determines the information relating to the cross-linking activity according to an intensity of light emitted by the cross-linking agent, and the image capturing system includes one or more filters to select for the light emitted by the cross-linking agent.

16. The system of claim 1, wherein the fluorescing cross-linking agent emits more than one wavelength, the one or more images captured by the image capture system include the more than one wavelength, and the information relating to the cross-linking activity is based on the one or more images including the more than one wavelength.

17. The system of claim 1, wherein the information relating to the cross-linking activity relates to an amount of the cross-linking agent used to generate the cross-linking activity.

18. The system of claim 1, wherein the cross-linking agent is riboflavin and the light from excitation source is ultraviolet light.

19. The system of claim 1, wherein the one or more images of the corneal tissue provides a profile of the corneal tissue corresponding to one half of the cornea.

20. The system of claim 1, further comprising a second image capture system that includes a second camera and a second lens, wherein:
- the second camera and the second lens are offset on a second side of the axis defined by the light;
- the second camera captures, via the second lens, one or more second images showing the fluorescing cross-linking agent in a second half of the corneal tissue disposed on the second side of the axis defined by the light;
- the second camera defines a second image plane;
- the second lens defines a second lens plane;
- the second lens plane is separate from the second image plane;
- the one or more second images are associated with a second focal plane defined by the second camera and the second lens; and
- the second camera and the second lens are oriented such that the second image plane, the second lens plane, and the second focal plane all intersect each other at a second common intersection, wherein the controller is configured to receive further the one or more second images and to provide information relating to cross-linking activity at varying depths across two halves of the corneal tissue based on one or more wavelengths emitted by the fluorescing cross-linking agent.

* * * * *